United States Patent
Sexton et al.

(10) Patent No.: US 11,084,884 B2
(45) Date of Patent: Aug. 10, 2021

(54) PLASMA KALLIKREIN BINDING PROTEINS AND USES THEREOF IN TREATING HEREDITARY ANGIOEDEMA

(71) Applicant: Takeda Pharmaceutical Company Limited, Osaka (JP)

(72) Inventors: Daniel J. Sexton, Melrose, MA (US); Burt Adelman, Concord, MA (US); Yung Chyung, Lexington, MA (US); Christopher TenHoor, Hopkinton, MA (US); Jon A. Kenniston, Hingham, MA (US); Ryan Faucette, Melrose, MA (US); Ryan Iarrobino, Sterling, MA (US); Joseph Biedenkapp, Newton, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 537 days.

(21) Appl. No.: 15/113,297

(22) PCT Filed: Jan. 21, 2015

(86) PCT No.: PCT/US2015/012212
§ 371 (c)(1),
(2) Date: Jul. 21, 2016

(87) PCT Pub. No.: WO2015/112578
PCT Pub. Date: Jul. 30, 2015

(65) Prior Publication Data
US 2017/0002094 A1 Jan. 5, 2017

Related U.S. Application Data

(60) Provisional application No. 62/021,397, filed on Jul. 7, 2014, provisional application No. 61/944,361, filed on Feb. 25, 2014, provisional application No. 61/929,716, filed on Jan. 21, 2014.

(51) Int. Cl.
*C07K 16/40* (2006.01)
*A61K 39/00* (2006.01)

(52) U.S. Cl.
CPC ........ *C07K 16/40* (2013.01); *A61K 2039/505* (2013.01); *A61K 2039/545* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,045,452 A | 9/1991 | Spragg et al. |
| 5,444,156 A | 8/1995 | Veloso et al. |
| 8,816,055 B2 | 8/2014 | Sexton et al. |
| 8,822,653 B2 | 9/2014 | Sexton et al. |
| 9,266,964 B2 | 2/2016 | Sexton et al. |
| 10,336,832 B2 | 7/2019 | Sexton et al. |
| 10,370,453 B2 | 8/2019 | Sexton et al. |
| 10,428,158 B2 | 10/2019 | Conley et al. |
| 2003/0138417 A1 | 7/2003 | Kaisheva et al. |
| 2007/0253949 A1 | 11/2007 | Golz et al. |
| 2009/0105142 A1 | 4/2009 | Moscicki |
| 2010/0285507 A1 | 11/2010 | Cho et al. |
| 2011/0200611 A1 | 8/2011 | Sexton |
| 2012/0201756 A1 | 8/2012 | Sexton |
| 2012/0264798 A1 | 10/2012 | Sinha et al. |
| 2014/0335023 A1 | 11/2014 | Sexton et al. |
| 2015/0274841 A1 | 10/2015 | Conley et al. |
| 2015/0362492 A1 | 12/2015 | Joseph et al. |
| 2016/0017055 A1 | 1/2016 | Nixon et al. |
| 2016/0102150 A1 | 4/2016 | Sexton et al. |
| 2018/0002447 A1 | 1/2018 | Sexton et al. |
| 2018/0002448 A1 | 1/2018 | Sexton et al. |
| 2018/0002449 A1 | 1/2018 | Sexton et al. |
| 2018/0037664 A1 | 2/2018 | Sexton et al. |
| 2018/0037665 A1 | 2/2018 | Sexton et al. |
| 2018/0037666 A1 | 2/2018 | Sexton et al. |
| 2018/0298110 A1 | 10/2018 | Chyung et al. |
| 2018/0362664 A1 | 12/2018 | Adelman et al. |
| 2019/0185580 A1 | 6/2019 | Nixon et al. |

FOREIGN PATENT DOCUMENTS

| CN | 1233256 A | 10/1999 |
| CN | 101928346 A | 12/2010 |
| JP | 2009-529553 A | 8/2009 |
| JP | 2013-516478 A | 5/2013 |
| WO | WO 87/05396 A1 | 9/1987 |
| WO | WO 2006/036860 A2 | 4/2006 |
| WO | WO 2007/104541 A2 | 9/2007 |
| WO | WO 2011/085103 | 7/2011 |
| WO | WO 2014/113701 A1 | 7/2014 |
| WO | WO 2014/113712 A1 | 7/2014 |
| WO | WO 2014/152232 A2 | 9/2014 |

(Continued)

OTHER PUBLICATIONS

U.S. Appl. No. 14/773,766, filed Sep. 9, 2015, Published, 2016-0017055.
U.S. Appl. No. 13/345,170, filed Jan. 6, 2012, Granted, U.S. Pat. No. 8,816,055.
U.S. Appl. No. 14/310,814, filed Jun. 20, 2014, Granted, U.S. Pat. No. 9,266,964.
U.S. Appl. No. 14/969,498, filed Dec. 15, 2015, Published, 2016-0102150.
U.S. Appl. No. 12/985,914, filed Jan. 6, 2011, Granted, U.S. Pat. No. 8,822,653.
U.S. Appl. No. 14/339,053, filed Jul. 23, 2014, Published, 2014-0335023.
U.S. Appl. No. 15/706,622, filed Sep. 15, 2017, Published, 2018-0037665.

(Continued)

*Primary Examiner* — Sharon X Wen
(74) *Attorney, Agent, or Firm* — Wolf, Greenfield & Sacks, P.C.

(57) ABSTRACT

Provided herein are plasma kallikrein binding proteins such as antibodies binding to active plasma kallikrein and methods of using such proteins in treating hereditary angioedema.

17 Claims, 12 Drawing Sheets

Specification includes a Sequence Listing.

(56) References Cited

FOREIGN PATENT DOCUMENTS

| WO | WO 2015/112578 A1 | 7/2015 |
|---|---|---|
| WO | WO 2016/160926 A1 | 10/2016 |

OTHER PUBLICATIONS

U.S. Appl. No. 15/706,631, filed Sep. 15, 2017, Published, 2018-0037666.
U.S. Appl. No. 15/706,613, filed Sep. 15, 2017, Published, 2018-0037664.
U.S. Appl. No. 15/706,603, filed Sep. 15, 2017, Published, 2018-0002447.
U.S. Appl. No. 15/706,621, filed Sep. 15, 2017, Published, 2018-0002448.
U.S. Appl. No. 15/706,623, filed Sep. 15, 2017, Published, 2018-0002449.
U.S. Appl. No. 14/669,607, filed Mar. 26, 2015, Published, 2015-0274841.
U.S. Appl. No. 15/562,671, filed Sep. 28, 2017, Pending.
U.S. Appl. No. 16/061,103, filed Jun. 11, 2018, Pending.
EP 15740774.3, Jul. 24, 2017, Supplementary European Search Report.
PCT/US2015/012212, Apr. 9, 2015, International Search Report and Written Opinion.
PCT/US2015/012212, Aug. 4, 2016, International Preliminary Report on Patentability.
[No Author Listed] Dyax's DX-2930 granted Orphan Drug designation in hereditary angioedema. Dec. 6, 2013.
[No Author Listed] Fair Disclosure Wire, "Dyax Corp. announces positive results from phase 1a clinical trial of DX2930" dated Feb. 25, 2014. Last accessed from http://dialog.proquest.com/professional/printviewfile?accountid=157282 on May 20, 2016. p. 1-15.
Bagdasarian et al., Immunochemical studies of plasma kallikrein. J Clin Invest. Dec. 1974;54(6):1444-54.
Breedweld, Therapeutic monoclonal antibodies. Lancet. Feb. 26, 2000;355(9205):735-40. Review.
Casset et al., A peptide mimetic of an anti-CD4 monoclonal antibody by rational design. Biochem Biophys Res Commun. Jul. 18, 2003;307(1):198-205.
Chyung et al., A phase 1 study investigating DX-2930 in healthy subjects. Ann Allergy Asthma Immunol. Oct. 2014;113(4):460-6.e2. doi: 10.1016/j.anai.2014.05.028. Epub Jun. 26, 2014.
Feener EP. Plasma kallikrein and diabetic macular edema. Curr Diab Rep. Aug. 2010;10(4):270-5. doi: 10.1007/s11892-010-0127-1.
Ferrara et al., Recombinant renewable polyclonal antibodies. MAbs. 2015;7(1):32-41. doi: 10.4161/19420862.2015.989047.
Fink et al., Cellular expression of plasma prekallikrein in human tissues. Biol Chem. Sep. 2007;388(9):957-63.
Frank, 8. Hereditary angioedema. J Allergy Clin Immunol. Feb. 2008;121(2 Suppl):S398-401; quiz S419. doi: 10.1016/j.jaci.2007.07.057.
Gao et al., Extracellular carbonic anhydrase mediates hemorrhagic retinal and cerebral vascular permeability through prekallikrein activation. Nat Med. Feb. 2007;13(2):181-8. Epub Jan. 28, 2007.
Green, Antibody engineering via genetic engineering of the mouse: XenoMouse strains are a vehicle for the facile generation of therapeutic human monoclonal antibodies. J Immunol Methods. Dec. 10, 1999;231(1-2):11-23.
Kenniston et al., Discovery and Characterization of a Highly Specific Antibody Inhibitor of Plasma Kallikrein. Blood 2013;122:1067.
Kenniston et al., Inhibition of plasma kallikrein by a highly specific active site blocking antibody. J Biol Chem. Aug. 22, 2014;289(34):23596-608. doi: 10.1074/jbc.M114.569061. Epub Jun. 26, 2014.
Kettleborough et al., Humanization of a mouse monoclonal antibody by CDR-grafting: the importance of framework residues on loop conformation. Protein Eng. Oct. 1991;4(7):773-83.
Lederman et al., A Single Amino Acid Substitution in a Common African Allele of the CD4 Molecule Ablates Binding of the Monoclonal Antibody, OKT4. Molecular Immunology. 1991;28(11):1171-1181.
Levy et al., The therapeutic potential of a kallikrein inhibitor for treating hereditary angioedema. Expert Opin Investig Drugs. Sep. 2006;15(9):1077-90. Review.
Li et al., β-Endorphin omission analogs: Dissociation of immunoreactivity from other biological activities. Proc. Natl. Acad. Sci. USA. Jun. 1980;77(6):3211-3214.
Liu et al., Plasma kallikrein-kinin system and diabetic retinopathy. Biol Chem. Mar. 2013;394(3):319-28. doi: 10.1515/hsz-2012-0316.
Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.
Paul. Fv Structure and Diversity in Three Dimensions. Fundamental Immunology, 3rd Edition. 1993: 292-5.
Phipps et al., Plasma kallikrein mediates angiotensin II type 1 receptor-stimulated retinal vascular permeability. Hypertension. Feb. 2009;53(2):175-81. doi:10.1161/HYPERTENSIONAHA.108.117663. Epub Jan. 5, 2009. With 5 page Online Supplement.
Schneider et al., Critical role of kallikrein in hereditary angioedema pathogenesis: a clinical trial of ecallantide, a novel kallikrein inhibitor. J Allergy Clin Immunol. Aug. 2007;120(2):416-22. Epub Jun. 7, 2007.
Sexton et al., Comparison of Plasma Kallikrein Inhibition by the Endogenous C1-Inhibitor Versus DX-2930, a Monoclonal Antibody Inhibitor. Blood. 2013;122:1066.
Sexton et al., Discovery and characterization of fully human monoclonal antibody inhibitor of plasma kallikrein for the treatment of plasma kallikrein-mediated edema. J Allergy Clin Immunol. Feb. 2013;131(2):AB32. Suppl S(116). Annual meeting of the American Academy of Allergy, Asthma, and Immunology. San Antonio, TX, USA; Feb. 22-26.
Sexton et al., Specific inhibition of tissue kallikrein 1 with a human monoclonal antibody reveals a potential role in airway diseases. Biochem J. Aug. 13, 2009;422(2):383-92. doi: 10.1042/BJ20090010.
Tang et al., Expression, crystallization, and three-dimensional structure of the catalytic domain of human plasma kallikrein. J Biol Chem. Dec. 9, 2005;280(49):41077-89. Epub Sep. 30, 2005.
Veloso et al., A monoclonal anti-human plasma prekallikrein antibody that inhibits activation of prekallikrein by factor XIIa on a surface. Blood. Oct. 1987;70(4):1053-62.
Veronez et al., The involvement of proteoglycans in the human plasma prekallikrein interaction with the cell surface. PLoS One. Mar. 12, 2014;9(3):e91280. doi: 10.1371/journal.pone.0091280. eCollection 2014.
Weaver, Animal studies paint misleading picture. Nature International Weekly Journal of Science. Published online Mar. 30, 2010. Retrieved on Aug. 1, 2017 from http://www.nature.com/news.2010.158.html.
[No Author Listed] Shire Reports Positive Topline Phase 3 Results for Lanadelumab (SHP643) in Patients with Hereditary Angioedema. May 18, 2017. Retrieved from the Internet: http://investors.shire.com/~/media/Files/S/Shire-IR/presentations-webcast/year-2017/shire-investor-presentation-2017-05-18.pdf on Apr. 3, 2019. 10 pages.
Banerji et al., Inhibiting Plasma Kallikrein for Hereditary Angioedema Prophylaxis. N Engl J Med. Feb. 23, 2017;376(8):717-728. doi: 10.1056/NEJMoa1605767.
Bendig, Humanization of Rodent Monoclonal Antibodies by CDR Grafting. Companion to Methods in Enzymology. 1995;8:83-93.
Boyles, Novel Kallikrein Inhibitor Promising for HAE Prophylaxis. Med Page Today. Feb. 22, 2017. Retrieved from the Internet: https://www.medpagetoday.org/pulmonology/generalpulmonary/63342?vpass=1 on Apr. 3, 2019. 4 pages.
MacCallum et al., Antibody-antigen interactions: contact analysis and binding site topography. J Mol Biol. Oct. 11, 1996;262(5):732-45.
Okano et al., Chapter 9.1.2 Drug Action and Blood Concentration. Shin Yakuzaiaku Soron, revised 3rd Edition, Apr. 10, 1987:205-253.

(56) References Cited

OTHER PUBLICATIONS

U.S. Appl. No. 16/445,304, filed Jun. 19, 2019, Sexton et al.
U.S. Appl. No. 16/411,242, filed May 14, 2019, Sexton et al.
U.S. Appl. No. 16/541,743, filed Aug. 15, 2019, Conley et al.
Shariat-Madar et al., Assembly and activation of the plasma kallikrein/kinin system: a new interpretation. Int Immunopharmacol. Dec. 2002;2(13-14):1841-9.

SEQUENCE LISTING

```
<160> NUMBER OF SEQ ID NOS: 10

<210> SEQ ID NO 1
<211> LENGTH: 469
<212> TYPE: PRT
<213> ORGANISM: Artificial Sequence
<220> FEATURE:
<223> OTHER INFORMATION: Synthetic Polypeptide

<400> SEQUENCE: 1

Met Gly Trp Ser Cys Ile Leu Phe Leu Val Ala Thr Ala Thr Gly Ala
1               5                   10                  15
```

-continued

His Ser Glu Val Gln Leu Leu Glu Ser Gly Gly Gly Leu Val Gln Pro
            20                  25                  30

Gly Gly Ser Leu Arg Leu Ser Cys Ala Ala Ser Gly Phe Thr Phe Ser
            35                  40                  45

His Tyr Ile Met Met Trp Val Arg Gln Ala Pro Gly Lys Gly Leu Glu
50                      55                  60

Trp Val Ser Gly Ile Tyr Ser Ser Gly Gly Ile Thr Val Tyr Ala Asp
65                      70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Tyr Arg Arg Ile Gly Val Pro Arg Arg Asp Glu Phe Asp
            115                 120                 125

Ile Trp Gly Gln Gly Thr Met Val Thr Val Ser Ser Ala Ser Thr Lys
130                     135                 140

Gly Pro Ser Val Phe Pro Leu Ala Pro Ser Ser Lys Ser Thr Ser Gly
145                     150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly
465

<210> SEQ ID NO 2
<211> LENGTH: 231
<212> TYPE: PRT
<213> ORGANISM: Artificial Sequence
<220> FEATURE:
<223> OTHER INFORMATION: Synthetic Polypeptide

<400> SEQUENCE: 2

Met Gly Trp Ser Cys Ile Leu Phe Leu Val Ala Thr Ala Thr Gly Ala
1               5                   10                  15

His Ser Asp Ile Gln Met Thr Gln Ser Pro Ser Thr Leu Ser Ala Ser
            20                  25                  30

Val Gly Asp Arg Val Thr Ile Thr Cys Arg Ala Ser Gln Ser Ile Ser
        35                  40                  45

Ser Trp Leu Ala Trp Tyr Gln Gln Lys Pro Gly Lys Ala Pro Lys Leu
    50                  55                  60

Leu Ile Tyr Lys Ala Ser Thr Leu Glu Ser Gly Val Pro Ser Arg Phe
65                  70                  75                  80

Ser Gly Ser Gly Ser Gly Thr Glu Phe Thr Leu Thr Ile Ser Ser Leu
                85                  90                  95

Gln Pro Asp Asp Phe Ala Thr Tyr Tyr Cys Gln Gln Tyr Asn Thr Tyr
            100                 105                 110

Trp Thr Phe Gly Gln Gly Thr Lys Val Glu Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230

<210> SEQ ID NO 3
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ile Met Met Trp Val Arg Gln Ala Pro Gly Lys Gly Leu Glu Trp Val
            35                  40                  45

Ser Gly Ile Tyr Ser Ser Gly Gly Ile Thr Val Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Arg Arg Ile Gly Val Pro Arg Arg Asp Glu Phe Asp Ile Trp
                100                 105                 110

Gly Gln Gly Thr Met Val Thr Val Ser Ser
            115                 120

<210> SEQ ID NO 4
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 4

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Lys Ala Ser Thr Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile Lys
            100                 105

<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 5

His Tyr Ile Met Met
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 6

Gly Ile Tyr Ser Ser Gly Gly Ile Thr Val Tyr Ala Asp Ser Val Lys
1               5                   10                  15

Gly

```
<210> SEQ ID NO 7
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 7

Arg Arg Ile Gly Val Pro Arg Arg Asp Glu Phe Asp Ile
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 8

Arg Ala Ser Gln Ser Ile Ser Ser Trp Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 9

Lys Ala Ser Thr Leu Glu Ser
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 10

Gln Gln Tyr Asn Thr Tyr Trp Thr
1               5
```

PLASMA KALLIKREIN BINDING PROTEINS AND USES THEREOF IN TREATING HEREDITARY ANGIOEDEMA

CROSS-REFERENCE TO RELATED APPLICATIONS

This application is a national stage filing under 35 U.S.C. § 371 of international PCT application PCT/US2015/012212, filed Jan. 21, 2015, which claims priority to U.S. Provisional Application No. 61/929,716, filed Jan. 21, 2014, to U.S. Provisional Application No. 61/944,361, filed Feb. 25, 2014, and to U.S. Provisional Application No. 62/021,397 filed Jul. 7, 2014. The entire contents of each of these referenced applications are incorporated by reference herein.

BACKGROUND

Plasma kallikrein is a serine protease component of the contact system and a potential drug target for different inflammatory, cardiovascular, infectious (sepsis) and oncology diseases (Sainz I. M. et al., Thromb Haemost 98, 77-83, 2007). The contact system is activated by either factor XIIa upon exposure to foreign or negatively charged surfaces or on endothelial cell surfaces by prolylcarboxypeptidases (Sainz I. M. et al., Thromb Haemost 98, 77-83, 2007). Activation of the plasma kallikrein amplifies intrinsic coagulation via its feedback activation of factor XII and enhances inflammation via the production of the proinflammatory nonapeptide bradykinin. As the primary kininogenase in the circulation, plasma kallikrein is largely responsible for the generation of bradykinin in the vasculature. A genetic deficiency in the C1-inhibitor protein (C1-INH), the major natural inhibitor of plasma kallikrein, leads to hereditary angioedema (HAE). Patients with HAE suffer from acute attacks of painful edema often precipitated by unknown triggers (Zuraw B. L. et al., N Engl J Med 359, 1027-1036, 2008).

SUMMARY

The present disclosure is, in part, based on the unexpected results derived from pharmacokinetic studies and pharmacokinetic modeling, showing that doses of an antibody binding to the active form of human plasma kallikrein (e.g., 100 mg to 300 mg) that maintains the plasma concentration of the antibody above 80 nM would be sufficient to show beneficial (e.g., prophylactic) effect in treating hereditary angioedema. Further, administering DX-2930 at the amount of 100 mg every 2 weeks or at the amount of 300 mg every 4 weeks would maintain a steady state plasma drug concentration of above 80 nM and administering DX-2930 at the amount of 300 mg every 2 weeks would maintain a stead plasma drug concentration of above 200 nM.

The present disclosure is also based, in part, on the unexpected discovery that an antibody binding to the active form of human plasma kallikrein exhibited superior therapeutic effects in treating hereditary angioedema (HAE) at various doses (0.1 mg/kg, 0.3 mg/kg, 1 mg/kg, or 3 mg/kg) without evidence of dose-limiting toxicity at single doses up to 3.0 mg/kg. Pharmacokinetic results demonstrated that DX-2930 has linear, dose-dependent exposure and a mean elimination half-life of 17 to 20 days across dose groups, following a single injection to healthy subjects. Pharmacodynamic results from two different exploratory biomarker assays confirmed ex vivo plasma kallikrein inhibition in a dose and time dependent manner.

Accordingly, one aspect of the present disclosure features a method of treating HAE (e.g., type I, II, or III), the method comprising administering to a subject in need thereof an antibody that binds the active form of pKal in an effective amount (e.g., 100 mg to 400 mg or 100 to 300 mg) such that the plasma concentration of the antibody in the subject is above about 80 nM. In some embodiments, the antibody (e.g., DX-2930) is administered at 100 mg every two weeks. In some embodiments, the antibody (e.g., DX-2930) is administered at 300 mg every 2 weeks or every 4 weeks.

Another aspect of the present disclosure features a method of treating HAE (e.g., type I, II, or III), the method comprising (a) administering to a subject in need thereof an antibody (e.g., a full-length antibody or an antigen-binding fragment thereof) that binds active plasma kallikrein at a first dosage; (b) measuring the plasma concentration of the antibody in the subject; and (c) administering to the subject the antibody at a second dosage if the plasma concentration of the antibody is lower than about 80 nM. In some embodiments, the first dosage, the second dosage, or both are 100 mg to 400 mg or 100 mg to 300 mg (e.g., 100 mg or 300 mg of DX-2930). In some embodiments, the second dosage is higher than the first dosage.

Accordingly, one aspect of the present disclosure features a method of treating HAE (e.g., type I, II, or III), the method comprising: administering a single dose of an isolated antibody to a subject in need thereof, wherein the antibody (e.g., a full-length antibody or an antigen-binding fragment thereof) binds active plasma kallikrein (e.g., does not bind prekallikrein). Optionally, the method further comprises monitoring the level of creatine phosphokinase in the subject before and after the treatment. In some embodiments, the single dose of any of the antibodies described herein is 0.1-3 mg/kg (e.g., 0.1 mg/kg, 0.3 mg/kg, 1 mg/kg, or 3 mg/kg).

In another aspect, the present disclosure provides a method of treating hereditary HAE, the method comprising: administering to a subject in need thereof a plurality of doses of an isolated antibody (e.g., a full length antibody or an antigen-binding fragment thereof) that binds active plasma kallikrein (e.g., an antibody that binds the active human plasma kallikrein but not human prekallikrein), wherein each of the two consecutive doses are at least 2 weeks apart (e.g., 3 weeks, 4 weeks, 5 weeks, or 6 weeks apart). In some embodiments, at least one dose of the plurality of doses is 0.1-3 mg/kg. For example, each of the doses of the plurality of doses is 3 mg/kg. In some examples, the antibody is administered monthly (e.g., every 28 days) for, e.g., 6 months.

In yet another aspect, the present disclosure features a method of treating HAE, the method comprising: (i) administering to a subject in need thereof one or more doses of an isolated antibody (e.g., a full length antibody or an antigen-binding fragment thereof) that binds active plasma kallikrein (e.g., an antibody that binds human active plasma kallikrein but not human prekallikrein), (ii) measuring the inhibition level of plasma kallikrein by the antibody in the subject after the last dose, and (iii) administering to the subject a further dose of the antibody if the inhibition level is lower than a minimum therapeutic level. In some embodiments, the one or more doses are 0.1-3 mg/kg (e.g., 0.1 mg/kg, 0.3 mg/kg, 1 mg/kg, or 3 mg/kg for each of the doses). In one example, the minimum therapeutic level represents a serum or plasma concentration of the antibody lower than about 80 nM.

In any of the methods described herein, the anti-pallikrein antibody may be a full-length antibody or an antigen-binding fragment thereof. In some embodiments, the antibody binds active plasma kallikrein and does not bind prekallikrein.

In some embodiments of any one of the methods described herein, the antibody binds to the same epitope as DX-2930 or competes against DX-2930 for binding to the active plasma kallikrein. In some embodiments, the antibody comprises the same heavy chain CDRs as DX-2930, the same light chain CDRs as DX-2930, or both. In some embodiments, the antibody is DX-2930, which is a full-length IgG antibody as described herein, or an antigen-binding fragment thereof.

In some embodiments of any one of the methods described herein, the antibody can be administered by subcutaneous administration. In some embodiments, the subject is a human patient suffering from, suspected of having, or at risk for HAE attack. For example, the method described herein is for prophylactic treatment of HAE.

In some embodiments of any one of the methods described herein, the method further comprises monitoring the level of creatine phosphokinase in the subject before and after the treatment, or during the course of the treatment. If creatine phosphokinase elevation is observed, the doses of the antibody (e.g., DX-2930) may be reduced or the treatment may be terminated.

In yet another aspect, the present disclosure provides a method for determining an optimal dosage (e.g., an optimal prophylactic dosage) of treating hereditary angioedema (HAE) in a subject, the method comprising (a) administering (e.g., subcutaneously) to a subject in need thereof any of the antibodies described herein that binds active plasma kallikrein (e.g., DX-2930 or an antigen-binding fragment thereof) at an initial dosage; (b) measuring the plasma concentration of the antibody in the subject; and (c) increasing the dosage of the antibody if the plasma concentration of the antibody is lower than about 80 nM; wherein a dosage that maintains the plasma concentration of the antibody above about 80 nM is chosen as the optimal prophylaxis dosage for the subject. In some embodiments, the subject is a human patient who does not exhibit HAE symptoms at the time the antibody is administered. In some embodiments, the initial dosage is about 100 mg to 400 mg or 100 mg to 300 mg (e.g., 100 mg or 300 mg of DX-2930).

The method described above may further comprise monitoring the level of creatine phosphokinase in the subject before and after the treatment, or during the course of the treatment. In addition, the method may further comprise reducing the dosage of the antibody or terminating the treatment if creatine phosphokinase elevation is observed.

In any of the methods described herein the plasma concentration of the antibody can be measured by a plasma kallikrein activity assay or an immune assay.

Also within the scope of the present disclosure are (a) pharmaceutical compositions for use in treating HAE or determining optimal dosage of an agent for treating HAE, the pharmaceutical composition comprising any of the anti-kallikrein antibodies described herein and a pharmaceutically acceptable carrier, and (b) use of the pharmaceutical composition for manufacturing a medicament for the treatment of HAE. Use of the antibodies for the intended purposes could be performed under the dosing conditions as described herein.

The details of one or more embodiments of the invention are set forth in the description below. Other features or advantages of the present invention will be apparent from the following drawings and detailed description of several embodiments, and also from the appended claims.

DETAILED DESCRIPTION

Definitions

Figure 1:
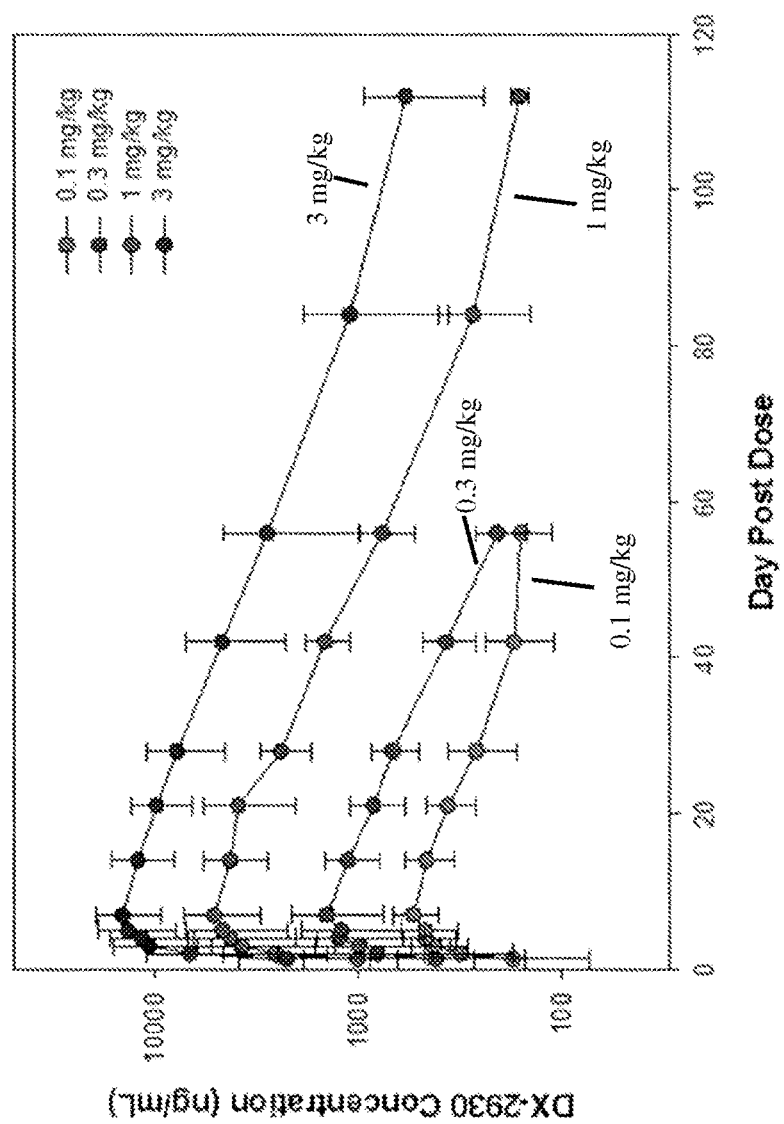
FIG. 1 is a graph showing the mean DX-2930 concentration following subcutaneous (SC) administration to healthy subjects. Concentration-time plots for each dose cohort are displayed on a log scale. The error bars are standard deviations. The profiles demonstrate a linear, dose dependent exposure. The parallel elimination phases across dose groups are consistent with a well behaved antibody with dose-independent kinetics in that all doses behave in a uniform manner.

For convenience, before further description of the present invention, certain terms employed in the specification, examples and appended claims are defined here. Other terms are defined as they appear in the specification.

The singular forms "a", "an", and "the" include plural references unless the context clearly dictates otherwise.

The term "antibody" refers to a protein that includes at least one immunoglobulin variable domain (variable region) or immunoglobulin variable domain (variable region) sequence. For example, an antibody can include a heavy (H) chain variable region (abbreviated herein as VH or HV), and a light (L) chain variable region (abbreviated herein as VL or LV). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J Immunol. 1996; 26(3):629-39)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDRs"), interspersed with regions that are more conserved, termed "framework regions" ("FRs"). The extent of the framework region and CDRs have been defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain such that one or more CDR regions are positioned in a conformation suitable for an antigen binding site. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form an antigen binding site, e.g., a structure that preferentially interacts with plasma kallikrein.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and/or LC CDR3. Each of the light chain (LC) and/or heavy chain (HC) CDRs can be human. HC CDR3 can be human. One or more of the framework regions can be human, e.g., FR1, FR2, FR3, and/or FR4 of the HC and/or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, and/or CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody and that retain functionality include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refers to a preparation of antibodies or fragments thereof of single molecular composition, irrespective of how the antibody was generated.

Antibodies are "germlined" by reverting one or more non-germline amino acids in framework regions to corresponding germline amino acids of the antibody, so long as binding properties are substantially retained.

The inhibition constant (Ki) provides a measure of inhibitor potency; it is the concentration of inhibitor required to reduce enzyme activity by half and is not dependent on enzyme or substrate concentrations. The apparent Ki ($K_{i,app}$) is obtained at different substrate concentrations by measuring the inhibitory effect of different concentrations of inhibitor (e.g., inhibitory binding protein) on the extent of the reaction (e.g., enzyme activity); fitting the change in pseudo-first order rate constant as a function of inhibitor concentration to the Morrison equation (Equation 1) yields an estimate of the apparent Ki value. The Ki is obtained from the y-intercept extracted from a linear regression analysis of a plot of Ki,app versus substrate concentration.

$$v = v_o - v_o \left( \frac{(K_{i,app} + I + E) - \sqrt{(K_{i,app} + I + E)^2 - 4 \cdot I \cdot E}}{2 \cdot E} \right) \quad \text{Equation 1}$$

Where v=measured velocity; $v_0$=velocity in the absence of inhibitor; $K_{i,app}$=apparent inhibition constant; I=total inhibitor concentration; and E=total enzyme concentration.

As used herein, "binding affinity" refers to the apparent association constant or $K_A$. The $K_A$ is the reciprocal of the dissociation constant ($K_D$). A binding antibody may, for example, have a binding affinity of at least $10^5$, $10^6$, $10^7$, $10^8$, $10^9$, $10^{10}$ and $10^{11}$ M$^{-1}$ for a particular target molecule, e.g., plasma kallikrein. Higher affinity binding of a binding antibody to a first target relative to a second target can be indicated by a higher $K_A$ (or a smaller numerical value $K_D$) for binding the first target than the $K_A$ (or numerical value $K_D$) for binding the second target. In such cases, the binding antibody has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

[Bound]=$N$·[Free]/((1/$K_A$)+[Free]).

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term "binding antibody" (or "binding protein" used interchangeably herein) refers to a antibody that can interact with a target molecule. This term is used interchangeably with "ligand." A "plasma kallikrein binding antibody" refers to an antibody that can interact with (e.g., bind) plasma kallikrein, and includes, in particular, antibodies that preferentially or specifically interact with and/or inhibit plasma kallikrein. An antibody inhibits plasma kallikrein if it causes a decrease in the activity of plasma kallikrein as compared to the activity of plasma kallikrein in the absence of the antibody and under the same conditions.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

It is possible for one or more framework and/or CDR amino acid residues of a binding protein to include one or more mutations (e.g., substitutions (e.g., conservative substitutions or substitutions of non-essential amino acids), insertions, or deletions) relative to a binding protein described herein. A plasma kallikrein binding protein may have mutations (e.g., substitutions (e.g., conservative substitutions or substitutions of non-essential amino acids), insertions, or deletions) (e.g., at least one, two, three, or four, and/or less than 15, 12, 10, 9, 8, 7, 6, 5, 4, 3, or 2 mutations) relative to a binding protein described herein, e.g., mutations which do not have a substantial effect on protein function. The mutations can be present in framework regions, CDRs, and/or constant regions. In some embodiments, the mutations are present in a framework region. In some embodiments, the mutations are present in a CDR. In some embodiments, the mutations are present in a constant region. Whether or not a particular substitution will be tolerated, i.e., will not adversely affect biological properties, such as binding activity, can be predicted, e.g., by evaluating whether the mutation is conservative or by the method of Bowie, et al. (1990) Science 247:1306-1310.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

A first binding antibody "binds to the same epitope" as a second binding antibody if the first binding antibody binds to the same site on a target compound that the second binding antibody binds, or binds to a site that overlaps (e.g., 50%, 60%, 70%, 80%, 90%, or 100% overlap, e.g., in terms of amino acid sequence or other molecular feature (e.g., glycosyl group, phosphate group, or sulfate group)) with the site that the second binding antibody binds.

A first binding antibody "competes for binding" with a second binding antibody if the binding of the first binding antibody to its epitope decreases (e.g., by 10%, 20%, 30%, 40%, 50%, 60%, 70%, 80%, 90%, 100%, or more) the amount of the second binding antibody that binds to its epitope. The competition can be direct (e.g., the first binding antibody binds to an epitope that is the same as, or overlaps with, the epitope bound by the second binding antibody), or indirect (e.g., the binding of the first binding antibody to its epitope causes a steric change in the target compound that decreases the ability of the second binding antibody to bind to its epitope).

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

A "humanized" immunoglobulin variable region is an immunoglobulin variable region that is modified to include a sufficient number of human framework amino acid positions such that the immunoglobulin variable region does not elicit an immunogenic response in a normal human Descriptions of "humanized" immunoglobulins include, for example, U.S. 6,407,213 and U.S. 5,693,762.

An "isolated" antibody refers to an antibody that is removed from at least 90% of at least one component of a natural sample from which the isolated antibody can be obtained. Antibodies can be "of at least" a certain degree of purity if the species or population of species of interest is at least 5, 10, 25, 50, 75, 80, 90, 92, 95, 98, or 99% pure on a weight-weight basis.

A "patient," "subject" or "host" (these terms are used interchangeably) to be treated by the subject method may mean either a human or non-human animal.

The terms "prekallikrein" and "preplasma kallikrein" are used interchangeably herein and refer to the zymogen form of active plasma kallikrein, which is also known as prekallikrein.

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher. In some embodiments, a plasma kallikrein binding antibody can have about 85%, 90%, 91%, 92%, 93%, 94%, 95%, 96%, 97%, 98%, 99% or higher sequence identity to an antibody described herein. In some embodiments, a plasma kallikrein binding antibody can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to an antibody described herein (e.g., DX-2930). In some embodiments, a plasma kallikrein binding antibody can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to an antibody described herein (e.g., DX-2930). In some embodiments, a plasma kallikrein binding antibody can have about 85%, 90%, 91%, 92%, 93%, 94%, 95%, 96%, 97%, 98%, 99% or higher sequence identity in the constant region (e.g., CHL CH2, CH3, and/or CL1) to an antibody described herein (e.g., DX-2930).

In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding that are statistically significant (e.g., P value<0.05 or 0.02). The terms "induce", "inhibit", "potentiate", "elevate", "increase", "decrease" or the like, e.g., which denote distinguishable qualitative or quantitative differences between two states, may refer to a difference, e.g., a statistically significant difference, between the two states.

A "therapeutically effective dosage" preferably modulates a measurable parameter, e.g., plasma kallikrein activity, by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions. Alternatively, this property of a composition can be evaluated by examining the ability of the compound to modulate a parameter in vitro.

The term "treating" as used herein refers to the application or administration of a composition including one or more active agents to a subject, who has an allergic disease, a symptom of the allergic disease, or a predisposition toward the allergic disease, with the purpose to cure, heal, alleviate, relieve, alter, remedy, ameliorate, improve, or affect the disease, the symptoms of the disease, or the predisposition toward the disease. "Prophylactic treatment," also known as "preventive treatment," refers to a treatment that aims at protecting a person from, or reducing the risk for a disease to which he or she has been, or may be, exposed.

The term "preventing" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Plasma Kallikrein Binding Antibodies

Plasma kallikrein binding antibodies for use in the methods described herein can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')2 or scFv fragment. The binding antibody can include two heavy chain immunoglobulins and two light chain immunoglobulins, or can be a single chain antibody. Plasma kallikrein binding antibodies can be recombinant proteins such as humanized, CDR grafted, chimeric, deimmunized, or in vitro generated antibodies, and may optionally include constant regions derived from human germline immunoglobulin sequences. In one embodiment, the plasma kallikrein binding antibody is a monoclonal antibody.

In one aspect, the disclosure features an antibody (e.g., an isolated antibody) that binds to plasma kallikrein (e.g., human plasma kallikrein and/or murine kallikrein) and includes at least one immunoglobulin variable region. For example, the antibody includes a heavy chain (HC) immunoglobulin variable domain sequence and/or a light chain (LC) immunoglobulin variable domain sequence. In one embodiment, the antibody binds to and inhibits plasma kallikrein, e.g., human plasma kallikrein and/or murine kallikrein.

The antibody can include one or more of the following characteristics: (a) a human CDR or human framework region; (b) the HC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a HC variable domain described herein; (c) the LC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a LC variable domain described herein; (d) the LC immunoglobulin variable domain sequence is at least 85, 88, 89, 90, 91, 92, 93, 94, 95, 96, 97, 98, 99, or 100% identical to a LC variable domain described herein (e.g., overall or in framework regions or CDRs); (e) the HC immunoglobulin variable domain sequence is at least 85, 88, 89, 90, 91, 92, 93, 94, 95, 96, 97, 98, 99, or 100% identical to a HC variable domain described herein (e.g., overall or in framework regions or CDRs); (f) the antibody binds an epitope bound by an antibody described herein, or competes for binding with an antibody described herein; (g) a primate CDR or primate framework region; (h) the HC immunoglobulin variable domain sequence comprises a CDR1 that differs by at least one amino acid but by no more than 2 or 3 amino acids from the CDR1 of a HC variable domain described herein; (i) the HC immunoglobulin variable domain sequence comprises a CDR2 that differs by at least one amino acid but by no more than 2, 3, 4, 5, 6, 7, or 8 amino acids from the CDR2 of a HC variable domain described herein; (j) the HC immunoglobulin variable domain sequence comprises a CDR3 that differs by at least one amino acid but by no more than 2, 3, 4, 5, or 6 amino acids from the CDR3 of a HC variable domain described herein; (k) the LC immunoglobulin variable domain sequence comprises a CDR1 that differs by at least one amino acid but by no more than 2, 3, 4, or 5 amino acids from the CDR1 of a LC variable domain described herein; (1) the LC immunoglobulin variable domain sequence comprises a CDR2 that differs by at least one amino acid but by no more than 2, 3, or 4 amino acids from the CDR2 of a LC variable domain described herein; (m) the LC immunoglobulin variable domain sequence comprises a CDR3 that differs by at least one amino acid but by no more than 2, 3, 4, or 5 amino acids from the CDR3 of a LC variable domain described herein; (n) the LC immunoglobulin variable domain sequence differs by at least one amino acid but by no more than 2, 3, 4, 5, 6, 7, 8, 9, or 10 amino acids from a LC variable domain described herein (e.g., overall or in framework regions or CDRs); and (o) the HC immunoglobulin variable domain sequence differs by at least one amino acid but by no more than 2, 3, 4, 5, 6, 7, 8, 9, or 10 amino acids from a HC variable domain described herein (e.g., overall or in framework regions or CDRs).

The plasma kallikrein binding protein may be an isolated antibody (e.g., at least 70, 80, 90, 95, or 99% free of other proteins). In some embodiments, the plasma kallikrein binding antibody, or composition thereof, is isolated from antibody cleavage fragments (e.g., DX-2930) that are inactive or partially active (e.g., bind plasma kallikrein with a Ki, app of 5000 nM or greater) compared to the plasma kallikrein binding antibody. For example, the plasma kallikrein binding antibody is at least 70% free of such antibody cleavage fragments; in other embodiments the binding antibody is at least 80%, at least 90%, at least 95%, at least 99% or even 100% free from antibody cleavage fragments that are inactive or partially active.

The plasma kallikrein binding antibody may additionally inhibit plasma kallikrein, e.g., human plasma kallikrein.

In some embodiments, the plasma kallikrein binding antibody does not bind prekallikrein (e.g., human prekallikrein and/or murine prekallikrein), but binds to the active form of plasma kallikrein (e.g., human plasma kallikrein and/or murine kallikrein).

In certain embodiments, the antibody binds at or near the active site of the catalytic domain of plasma kallikrein, or a fragment thereof, or binds an epitope that overlaps with the active site of plasma kallikrein.

In some aspects, the antibody binds the same epitope or competes for binding with an antibody described herein.

The antibody can bind to plasma kallikrein, e.g., human plasma kallikrein, with a binding affinity of at least $10^5$, $10^6$, $10^7$, $10^8$, $10^9$, $10^{10}$ and $10^{11}$ M$^{-1}$. In one embodiment, the antibody binds to human plasma kallikrein with a $K_{off}$ slower than $1\times10^{-3}$, $5\times10^{-4}$ s$^{-1}$, or $1\times10^{-4}$ s$^{-1}$. In one embodiment, the antibody binds to human plasma kallikrein with a $K_{on}$ faster than $1\times10^2$, $1\times10^3$, or $5\times10^3$ M$^{-1}$s$^{-1}$. In one embodiment, the antibody binds to plasma kallikrein, but does not bind to tissue kallikrein and/or plasma prekallikrein (e.g., the antibody binds to tissue kallikrein and/or plasma prekallikrein less effectively (e.g., 5-, 10-, 50-, 100-, or 1000-fold less or not at all, e.g., as compared to a negative control) than it binds to plasma kallikrein.

In one embodiment, the antibody inhibits human plasma kallikrein activity, e.g., with a Ki of less than $10^{-5}$, $10^{-6}$, $10^{-7}$, $10^{-8}$, $10^{-9}$, and $10^{-10}$ M. The antibody can have, for example, an IC$_{50}$ of less than 100 nM, 10 nM, 1, 0.5, or 0.2 nM. For example, the antibody may modulate plasma kallikrein activity, as well as the production of Factor XIIa (e.g., from Factor XII) and/or bradykinin (e.g., from high-molecular-weight kininogen (HMWK)). The antibody may inhibit plasma kallikrein activity, and/or the production of Factor XIIa (e.g., from Factor XII) and/or bradykinin (e.g., from high-molecular-weight kininogen (HMWK)). The affinity of the antibody for human plasma kallikrein can be characterized by a $K_D$ of less than 100 nm, less than 10 nM, less than 5 nM, less than 1 nM, less than 0.5 nM. In one embodiment, the antibody inhibits plasma kallikrein, but does not inhibit tissue kallikrein (e.g., the antibody inhibits tissue kallikrein less effectively (e.g., 5-, 10-, 50-, 100-, or 1000-fold less or not at all, e.g., as compared to a negative control) than it inhibits plasma kallikrein.

In some embodiments, the antibody has an apparent inhibition constant ($K_{i,app}$) of less than 1000, 500, 100, 5, 1, 0.5 or 0.2 nM.

Plasma kallikrein binding antibodies may have their HC and LC variable domain sequences included in a single polypeptide (e.g., scFv), or on different polypeptides (e.g., IgG or Fab).

In one embodiment, the HC and LC variable domain sequences are components of the same polypeptide chain. In another, the HC and LC variable domain sequences are components of different polypeptide chains. For example, the antibody is an IgG, e.g., IgG1, IgG2, IgG3, or IgG4. The antibody can be a soluble Fab. In other implementations the antibody includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC::HSA+VH::CH1, HSA::LC+VH::CH1, or other appropriate construction.

In one embodiment, the antibody is a human or humanized antibody or is non-immunogenic in a human. For example, the antibody includes one or more human antibody framework regions, e.g., all human framework regions, or framework regions at least 85, 88, 89, 90, 91, 92, 93, 94, 95, 96, 97, 98, 99% identical to human framework regions. In one embodiment, the antibody includes a human Fc domain, or an Fc domain that is at least 95, 96, 97, 98, or 99% identical to a human Fc domain.

In one embodiment, the antibody is a primate or primatized antibody or is non-immunogenic in a human. For example, the antibody includes one or more primate antibody framework regions, e.g., all primate framework regions, or framework regions at least 85, 88, 89, 90, 91, 92, 93, 94, 95, 96, 97, 98, 99% identical to primate framework regions. In one embodiment, the antibody includes a primate Fc domain, or an Fc domain that is at least 95, 96, 97, 98, or 99% identical to a primate Fc domain. "Primate" includes humans (Homo sapiens), chimpanzees (Pan troglodytes and Pan paniscus (bonobos)), gorillas (Gorilla gorilla), gibons, monkeys, lemurs, aye-ayes (D aubentonia madagascariensis), and tarsiers.

In some embodiments, the affinity of the primate antibody for human plasma kallikrein is characterized by a $K_D$ of less than 1000, 500, 100, 10, 5, 1, 0.5 nM, e.g., less than 10 nM, less than 1 nM, or less than 0.5 nM.

In certain embodiments, the antibody includes no sequences from mice or rabbits (e.g., is not a murine or rabbit antibody).

In some embodiments, the antibody used in the methods described herein may be DX-2930 as described herein or a functional variant thereof, or an antibody that binds the same epitope as DX-2930 or competes against DX-2930 for binding to active plasma kallikrein.

In one example, a functional variant of DX-2930 comprises the same complementary determining regions (CDRs) as DX-2930. In another example, the functional variants of DX-2930 may contain one or more mutations (e.g., conservative substitutions) in the FRs of either the $V_H$ or the $V_L$ as compared to those in the $V_H$ and $V_L$ of DX-2930. Preferably, such mutations do not occur at residues which are predicted to interact with one or more of the CDRs, which can be determined by routine technology. In other embodiments, the functional variants described herein contain one or more mutations (e.g., 1, 2, or 3) within one or more of the CDR regions of DX-2930. Preferably, such functional variants retain the same regions/residues responsible for antigen-binding as the parent. In yet other embodiments, a functional variant of DX-2930 may comprise a $V_H$ chain that comprises an amino acid sequence at least 85% (e.g., 90%, 92%, 94%, 95%, 96%, 97%, 98%, or 99%) identical to that of the $V_H$ of DX-2930 and/or a $V_L$ chain that has an amino acid sequence at least 85% (e.g., 90%, 92%, 94%, 95%, 96%, 97%, 98%, or 99%) identical to that of the $V_L$ of DX-2930. These variants are capable of binding to the active form of plasma kallikrein and preferably do not bind to prekallikrein.

The "percent identity" of two amino acid sequences is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

Antibody Preparation

Antibodies capable of binding PKal as described herein can be made by any method known in the art. See, for example, Harlow and Lane, (1988) Antibodies: A Laboratory Manual, Cold Spring Harbor Laboratory, New York.

In some embodiments, antibodies specific to a target antigen (e.g., a human PKal or the catalytic domain thereof) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-PKal monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the PKal activity. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of PKal. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA, 86:10029-10033 (1989). In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to a PKal can be identified from the library following routine procedures. Positive clones can be subjected to further screening to identify those that inhibits PKal activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the PKal polypeptide have been replaced (swapped) with sequences from a closely related, but antigenically distinct protein (such as another member of the neurotrophin protein family) By assessing binding of the antibody to the mutant PKal (e.g., those mutants described in Example 2 below), the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Any of the suitable methods known in the art, e.g., the epitope mapping methods as described herein, can be applied to determine whether the anti-PKal antibody binds one or more of the specific residues/segments in the PKal as described herein. Further, the interaction of the antibody with one or more of those defined residues in PKal can be determined by routine technology. For example, a crystal structure can be determined following the method disclosed in Example 1 below and the distances between the residues in PKal and one or more residues in the antibody can be determined accordingly. Based on such distance, whether a specific residue in PKal interacts with one or more residues in the antibody can be determined. Further, suitable methods, such as competition assays and target mutagenesis assays can be applied to determine the preferential binding of a candidate anti-PKal antibody to the PKal as compared to another target such as a mutant PKal.

Alternatively, the anti-PKal antibodies can be identified from antibody libraries, such as display libraries following methods known in the art.

Once an anti-PKal antibody is identified using any of the methods known in the art and is confirmed to be an antibody suitable for use in the treatment described herein, such an antibody may be produced via standard recombinant nucleic acid methods.

Generally, a nucleic acid sequence encoding the protein is cloned into a nucleic acid expression vector. Of course, if the protein includes multiple polypeptide chains, each chain can be cloned into an expression vector, e.g., the same or different vectors, that are expressed in the same or different cells.

Some antibodies, e.g., Fabs, can be produced in bacterial cells, e.g., *E. coli* cells (see e.g., Nadkarni, A. et al., 2007

Protein Expr Purif 52(1):219-29). For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al., 2001, J. Immunol. Methods. 251:123-35; Schoonooghe S. et al., 2009 BMC Biotechnol. 9:70; Abdel-Salam, H A. et al., 2001 Appl Microbiol Biotechnol 56(1-2):157-64; Takahashi K. et al., 2000 Biosci Biotechnol Biochem 64(10):2138-44; Edqvist, J. et al., 1991 J Biotechnol 20(3):291-300), *Hanseula*, or *Saccharomyces*. One of skill in the art can optimize antibody production in yeast by optimizing, for example, oxygen conditions (see e.g., Baumann K., et al. 2010 BMC Syst. Biol. 4:141), osmolarity (see e.g., Dragosits, M. et al., 2010 BMC Genomics 11:207), temperature (see e.g., Dragosits, M. et al., 2009 J Proteome Res. 8(3):1380-92), fermentation conditions (see e.g., Ning, D. et al. 2005 J. Biochem. and Mol. Biol. 38(3): 294-299), strain of yeast (see e.g., Kozyr, A V et al. 2004 Mol Biol (Mosk) 38(6): 1067-75; Horwitz, A H. et al., 1988 Proc Natl Acad Sci USA 85(22):8678-82; Bowdish, K. et al. 1991 J Biol Chem 266(18):11901-8), overexpression of proteins to enhance antibody production (see e.g., Gasser, B. et al., 2006 Biotechol. Bioeng. 94(2):353-61), level of acidity of the culture (see e.g., Kobayashi H., et al., 1997 FEMS Microbiol Lett 152(2):235-42), concentrations of substrates and/or ions (see e.g., Ko J H. et al., 2996 Appl Biochem Biotechnol 60(1): 41-8). In addition, yeast systems can be used to produce antibodies with an extended half-life (see e.g., Smith, B J. et al. 2001 Bioconjug Chem 12(5):750-756), In one preferred embodiment, antibodies are produced in mammalian cells. Preferred mammalian host cells for expressing the clone antibodies or antigen-binding fragments thereof include Chinese Hamster Ovary (CHO cells) (including dhfr- CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601 621), lymphocytic cell lines, e.g., NSO myeloma cells and SP2 cells, COS cells, HEK293T cells (J. Immunol. Methods (2004) 289(1-2):65-80), and a cell from a transgenic animal, e.g., a transgenic mammal. For example, the cell is a mammary epithelial cell.

In some embodiments, plasma kallikrein binding antibodies are produced in a plant or cell-free based system (see e.g., Galeffi, P., et al., 2006 J Transl Med 4:39).

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, Adv. Immunol. 51:1-84; Jefferis et al., 1998, Immunol. Rev. 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Pharmaceutical Compositions

One or more of the antibodies described herein can be present in a composition, e.g., a pharmaceutically acceptable composition or pharmaceutical composition. The plasma kallikrein binding antibody can be formulated together with a pharmaceutically acceptable carrier. In some embodiments, 100 mg to 300 mg of an antibody described herein (e.g., DX-2930 at a dosage of 100 mg or 300 mg) are present in a composition optionally with a pharmaceutically acceptable carrier, e.g., a pharmaceutically acceptable composition or pharmaceutical composition.

A pharmaceutically acceptable carrier includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal, or epidermal administration (e.g., by injection or infusion), although carriers suitable for inhalation and intranasal administration are also contemplated.

A pharmaceutically acceptable salt is a salt that retains the desired biological activity of the compound and does not impart any undesired toxicological effects (see e.g., Berge, S. M., et al., 1977, J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like.

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Many compositions are in the form of injectable or infusible solutions, such as compositions similar to those used for administration of humans with antibodies. An exemplary mode of administration is parenteral (e.g., intravenous, subcutaneous, intraperitoneal, intramuscular). In one embodiment, the plasma kallikrein binding protein is administered by intravenous infusion or injection. In another preferred embodiment, the plasma kallikrein binding protein is administered by intramuscular or subcutaneous injection. In another preferred embodiment, the plasma kallikrein binding protein is administered by intraperitoneal injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable to high drug concentration. Sterile injectable solutions can be prepared by incorporating the binding protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A plasma kallikrein binding antibody can be administered by a variety of methods, including intravenous injection or infusion. For example, for some herapeutic applications, the plasma kallikrein binding protein can be administered by intravenous infusion at a rate of less than 30, 20, 10, 5, or 1 mg/min to reach a dose of about 1 to 100 mg/m$^2$ or 7 to 25 mg/m$^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are available. See, e.g., Sustained and Controlled Release Drug Delivery Systems, J. R. Robinson, ed., 1978, Marcel Dekker, Inc., New York.

Pharmaceutical compositions can be administered with medical devices. For example, in one embodiment, a pharmaceutical composition disclosed herein can be administered with a device, e.g., a needleless hypodermic injection device, a pump, or implant.

In certain embodiments, a plasma kallikrein binding protein can be formulated to ensure proper distribution in vivo. For example, the blood-brain barrier (BBB) excludes many highly hydrophilic compounds. To ensure that the therapeutic compounds disclosed herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade, 1989, J. Clin. Pharmacol. 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody described herein is 0.1-20 mg/kg, more preferably 1-10 mg/kg. An anti- plasma kallikrein antibody can be administered, e.g., by intravenous infusion, e.g., at a rate of less than 30, 20, 10, 5, or 1 mg/min to reach a dose of about 1 to 100 mg/m$^2$ or about 5 to 30 mg/m$^2$. Dosage values may vary with the type and severity of the condition to be alleviated. For a particular subject, specific dosage regimens can be adjusted over time according to the individual need and the professional judgment of the person administering or supervising the administration of the compositions.

In some embodiments, the therapeutically or prophylactically effective amount of an antibody described herein (e.g., DX-2930) is 30 to 400 mg, 30 to 300 mg, 30 to 250 mg, 30 to 200 mg, 30 to 150 mg, 30 to 100 mg, 30 to 50 mg, 50 to 400 mg, 50 to 300 mg, 50 to 250 mg, 50 to 200 mg, 50 to 150 mg, 50 to 100 mg, 100 to 400 mg, 100 to 300 mg, 100 to 250 mg, 100 to 200 mg, 100 to 150 mg, 150 to 400 mg, 150 to 300 mg, 150 to 250 mg, 150 to 200 mg, 200 to 400 mg, 200 to 300 mg, 200 to 250 mg, 250 to 400 mg, 250 to 300 mg, or 300 to 400 mg, or any integer in between. In some embodiments, the therapeutically or prophylactically effective amount is 30 to 300 mg. In some embodiments, the therapeutically or prophylactically effective amount is 300 mg or more. In some embodiments, the therapeutically or prophylactically effective amount is 400 mg or more. In some embodiments, the therapeutically or prophylactically effective amount is 100 to 300 mg (100 mg, 150 mg, 200 mg. 250 mg. or 300 mg).

In some embodiments, the therapeutically or prophylactically effective amount of an antibody described herein (e.g., DX-2930) is 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, or 400 mg. In some embodiments, the therapeutically or prophylactically effective amount is 30 mg, 100 mg, or 300 mg. In some embodiments, the therapeutically or prophylactically effective amount is 100 mg or 300 mg. In some embodiments, the therapeutically or prophylactically effective amount is 100 mg. In some embodiments, the therapeutically or prophylactically effective amount is 300 mg.

In some embodiments, the therapeutically or prophylactically effective amount is administered at least two times, at least three times, at least four times, at least five times, at least six times, at least seven times, at least eight times, at least nine times, at least ten times, or more. In some embodiments, the therapeutically or prophylactically effective amount is administered daily, every other day, every third day, every fourth day, every fifth day, every sixth day, every week, every other week, every three weeks, every four weeks, every five weeks, every six weeks, every seven weeks, every eight weeks, or more. In some embodiments, the therapeutically or prophylactically effective amount is 100 mg or 300 mg and the amount is administered every two weeks or every four weeks. In some embodiments, the therapeutically or prophylactically effective amount is 100 mg and this amount of the antibody is administered every two weeks. In some embodiments, the therapeutically or prophylactically effective amount is 300 mg and this amount of the antibody is administered every two weeks or every four weeks. In some embodiments, the therapeutically or prophylactically effective amount is 300 mg and this amount of the antibody is administered every two weeks. In some embodiments, the therapeutically or prophylactically effective amount is 300 mg and the amount is administered every four weeks.

In some embodiments, the therapeutically or prophylactically effective amount is an amount that maintains a plasma or serum concentration of the antibody above about 80 nM (e.g., above 100 nm, above 150 nM, or about 200 nM). In some embodiments, the amount of the antibody is effective in maintaining the plasma or serum concentration of the antibody in the range of about 80-300 nM, e.g., 80-100 nM, 80-120 nM, 80-150 nM, 100-150 nM, 100-200 nM, 150-200 nM, or 200-300 nM. Plasma or serum concentration can be measured using a suitable assay, e.g., a plasma kallikrein activity assay such as those described herein, an immuno-based assay such as an ELISA assay or the Westernblot assay for determining cleaved kininogen as described herein, or by mass spectrometry.

The pharmaceutical compositions disclosed herein may include a "therapeutically effective amount" or a "prophylactically effective amount" of a plasma kallikrein binding protein disclosed herein.

Kits

One or more of the plasma kallikrein binding antibody described herein can be provided in a kit, e.g., as a component of a kit. For example, the kit includes (a) a plasma kallikrein binding antibody, e.g., a composition (e.g., a pharmaceutical composition) that includes a plasma kallikrein binding antibody, and, optionally (b) informational material. The informational material can be descriptive, instructional, marketing or other material that relates to a method described herein and/or the use of a plasma kallikrein binding antibody, e.g., for a method described herein. In some embodiments, the kit comprises one or more doses of a plasma kallikrein binding antibody, e.g., DX-2930. In some embodiments, the one or more doses are 100 mg or 300 mg.

The informational material of the kit is not limited in its form. In one embodiment, the informational material can include information about production of the compound, molecular weight of the compound, concentration, date of expiration, batch or production site information, and so forth. In one embodiment, the informational material relates to using the antibody to treat, prevent, or diagnosis of disorders and conditions, e.g., a plasma kallikrein associated disease or condition.

In one embodiment, the informational material can include instructions to administer a plasma kallikrein binding antibody in a suitable manner to perform the methods described herein, e.g., in a suitable dose, dosage form, mode of administration or dosing schedule (e.g., a dose, dosage form, dosing schedule or mode of administration described herein). In another embodiment, the informational material can include instructions to administer a plasma kallikrein binding antibody to a suitable subject, e.g., a human, e.g., a human having, or at risk for, a plasma kallikrein associated disease or condition. For example, the material can include instructions to administer a plasma kallikrein binding protein to a patient with a disorder or condition described herein, e.g., a plasma kallikrein associated disease, e.g., according to a dosing schedule described herein. The informational material of the kits is not limited in its form. In many cases, the informational material, e.g., instructions, is provided in print but may also be in other formats, such as computer readable material.

A plasma kallikrein binding antibody can be provided in any form, e.g., liquid, dried or lyophilized form. It is preferred that a plasma kallikrein binding antibody be substantially pure and/or sterile. When a plasma kallikrein binding antibody is provided in a liquid solution, the liquid solution preferably is an aqueous solution, with a sterile aqueous solution being preferred. When a plasma kallikrein binding antibody is provided as a dried form, reconstitution generally is by the addition of a suitable solvent. The solvent, e.g., sterile water or buffer, can optionally be provided in the kit.

The kit can include one or more containers for the composition containing a plasma kallikrein binding antibody. In some embodiments, the kit contains separate containers, dividers or compartments for the composition and informational material. For example, the composition can be contained in a bottle, vial, or syringe, and the informational material can be contained in association with the container. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a plasma kallikrein binding antibody. For example, the kit includes a plurality of syringes, ampules, foil packets, or blister packs, each containing a single unit dose of a plasma kallikrein binding antibody. The containers of the kits can be air tight, waterproof (e.g., impermeable to changes in moisture or evaporation), and/or light-tight.

The kit optionally includes a device suitable for administration of the composition, e.g., a syringe, or any such delivery device. In one embodiment, the device is an implantable device that dispenses metered doses of the antibody. The disclosure also features a method of providing a kit, e.g., by combining components described herein.

Treatment

In some aspects, the disclosure provides the use of antibodies that bind to active plasma kallikrein (e.g., human active plasma kallikrein) in treating HAE. Suitable antibodies for use in the treatment described herein include DX-2930 or a functional variant thereof as described herein, an antibody that binds the same epitope as DX-2930, or an antibody that competes against DX-2930 for binding to human active plasma kallikrein.

Hereditary Angioedema

Hereditary angioedema (HAE) is also known as "Quincke edema," C1 esterase inhibitor deficiency, C1 inhibitor deficiency, and hereditary angioneurotic edema (HANE). HAE is characterized by recurrent episodes of severe swelling (angioedema), which can affect, e.g., the limbs, face, genitals, gastrointestinal tract, and airway. Symptoms of HAE include, e.g., swelling in the arms, legs, lips, eyes, tongue, and/or throat; airway blockage that can involve throat swelling and sudden hoarseness; repeat episodes of abdominal cramping without obvious cause; and/or swelling of the intestines, which can be severe and can lead to abdominal cramping, vomiting, dehydration, diarrhea, pain, and/or shock. About one-third of individuals with this HAE develop a non-itchy rash called erythema marginatum during an attack.

Swelling of the airway can be life threatening and causes death in some patients. Mortality rates are estimated at 15-33%. HAE leads to about 15,000-30,000 emergency department visits per year.

Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm nih.gov/condition/hereditary-angioedema). The frequency and duration of attacks vary greatly among people with hereditary angioedema, even among people in the same family.

There are three types of HAE, known as types I, II, and III, all of which can be treated by the methods described herein. It is estimated that HAE affects 1 in 50,000 people, that type I accounts for about 85 percent of cases, type II accounts for about 15 percent of cases, and type III is very rare. Type III is the most newly described form and was originally thought to occur only in women, but families with affected males have been identified.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Without the proper levels of functional C1 inhibitor, excessive amounts of bradykinin are generated. Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III. The F12 gene provides instructions for making coagulation factor XII. In addition to playing a critical role in blood clotting (coagulation), factor XII is also an important stimulator of inflammation and is involved in the production of bradykinin Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When hereditary angioedema is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

C1 inhibitor therapies, as well as other therapies for HAE, are described in Kaplan, A. P., J Allergy Clin Immunol, 2010, 126(5):918-925.

Acute treatment of HAE attacks is provided to halt progression of the edema as quickly as possible. C1 inhibitor concentrate from donor blood, which is administered intravenously, is one acute treatment; however, this treatment is not available in many countries. In emergency situations where C1 inhibitor concentrate is not available, fresh frozen plasma (FFP) can be used as an alternative, as it also contains C1 inhibitor.

Purified C1 inhibitor, derived from human blood, has been used in Europe since 1979. Several C1 inhibitor treatments are now available in the U.S. and two C1 inhibitor products are now available in Canada. Berinert P (CSL Behring), which is pasteurized, was approved by the F.D.A. in 2009 for acute attacks. Cinryze (ViroPharma), which is nanofiltered, was approved by the F.D.A. in 2008 for prophylaxis. Rhucin (Pharming) is a recombinant C1 inhibitor under development that does not carry the risk of infectious disease transmission due to human blood-borne pathogens.

Treatment of an acute HAE attack also can include medications for pain relief and/or IV fluids.

Other treatment modalities can stimulate the synthesis of C1 inhibitor, or reduce C1 inhibitor consumption. Androgen medications, such as danazol, can reduce the frequency and severity of attacks by stimulating production of C1 inhibitor.

*Helicobacter pylori* can trigger abdominal attacks. Antibiotics to treat *h. pylori* will decrease abdominal attacks.

Newer treatments attack the contact cascade. Ecallantide (KALBITOR®, DX-88, Dyax) inhibits plasma kallikrein and has been approved in the U.S. Icatibant (FIRAZYR®, Shire) inhibits the bradykinin B2 receptor, and has been approved in Europe and the U.S.

Diagnosis of HAE can rely on, e.g., family history and/or blood tests. Laboratory findings associated with HAE types I, II, and III are described, e.g., in Kaplan, A. P., J Allergy Clin Immunol, 2010, 126(5):918-925. In type I HAE, the level of C1 inhibitor is decreased, as is the level of C4, whereas C1q level is normal. In type II HAE, the level of C1 inhibitor is normal or increased; however, C1 inhibitor function is abnormal. C4 level is decreased and C1q level is normal. In type III, the levels of C1 inhibitor, C4, and C1q can all be normal.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. Patient. 2012; 5(2):113-26.

Treating HAE with Anti-PKal Antibodies

The disclosure provides methods of treating (e.g., ameliorating, stabilizing, or eliminating one or more symptoms) of hereditary angioedema (HAE) by administering an antibody described herein (e.g., a therapeutically effective amount of an antibody described herein) to a subject having or suspected of having HAE, e.g., according to a dosing schedule described herein. Additionally provided are methods of treating HAE by administering an antibody described herein (e.g., a therapeutically effective amount of an antibody described herein), e.g., according to a dosing schedule described herein, or in combination with a second therapy, e.g., with one other agent, e.g., described herein. The disclosure also provides methods of preventing HAE or a symptom thereof by administering an antibody described herein (e.g., a prophylactically effective amount of an antibody described herein) to a subject at risk of developing HAE (e.g., a subject having a family member with HAE or a genetic predisposition thereto), e.g., according to a dosing schedule described herein. In some examples, the subject may be a human patient who has no HAE symptoms at the time of the treatment.

Antibodies that bind to plasma kallikrein, e.g., as described herein, have therapeutic and prophylactic utilities, particularly in human subjects. These antibodies are administered to a subject to treat, prevent, and/or diagnose a variety of disorders and conditions, including e.g., a plasma kallikrein associated disease, or even to cells in culture, e.g., in vitro or ex vivo. For example, these binding proteins can be used to modify the effects of plasma kallikrein released from cells in culture (Lilla et al., J. Biol Chem. 284(20): 13792-13803 (2009)). Treating includes administering an amount effective to alleviate, relieve, alter, remedy, ameliorate, improve or affect the disorder, the symptoms of the disorder or the predisposition toward the disorder. The treatment may also delay onset, e.g., prevent onset, or prevent deterioration of a disease or condition.

Methods of administering kallikrein binding antibodies and other agents are also described in "Pharmaceutical Compositions." Suitable dosages of the molecules used can depend on the age and weight of the subject and the particular drug used. The antibody can be used as competitive agents to inhibit, reduce an undesirable interaction, e.g., between plasma kallikrein and its substrate (e.g., Factor XII or HMWK). The dose of the antibody can be the amount sufficient to block 90%, 95%, 99%, or 99.9% of the activity of plasma kallikrein in the patient, especially at the site of disease. This may require 0.1, 1.0, 3.0, 6.0, or 10.0 mg/Kg. For an IgG having a molecular mass of 150,000 g/mole (two binding sites), these doses correspond to approximately 18 nM, 180 nM, 540 nM, 1.08 µM, and 1.8 µM of binding sites for a 5 L blood volume.

In one embodiment, the antibodies are used to inhibit an activity (e.g., inhibit at least one activity of plasma kallikrein, e.g., reduce Factor XIIa and/or bradykinin production) of plasma kallikrein, e.g., in vivo. The binding proteins can be used by themselves or conjugated to an agent, e.g., a cytotoxic drug, cytotoxin enzyme, or radioisotope.

The antibodies can be used directly in vivo to eliminate antigen-expressing cells via natural complement-dependent cytotoxicity (CDC) or antibody dependent cellular cytotoxicity (ADCC). The antibodies described herein can include complement binding effector domain, such as the Fc portions from IgG1, -2, or -3 or corresponding portions of IgM which bind complement. In one embodiment, a population of target cells is ex vivo treated with an antibody described herein and appropriate effector cells. The treatment can be supplemented by the addition of complement or serum containing complement. Further, phagocytosis of target cells coated with an antibody described herein can be improved by binding of complement proteins. In another embodiment target, cells coated with the antibody which includes a complement binding effector domain are lysed by complement.

Methods of administering plasma kallikrein binding antibodies are described in "Pharmaceutical Compositions." Suitable dosages of the molecules used will depend on the age and weight of the subject and the particular drug used. The antibodies can be used as competitive agents to inhibit or reduce an undesirable interaction, e.g., between a natural or pathological agent and the plasma kallikrein.

A therapeutically effective amount of an antibody as described herein, can be administered to a subject having, suspected of having, or at risk for HAE, thereby treating (e.g., ameliorating or improving a symptom or feature of a disorder, slowing, stabilizing and/or halting disease progression) the disorder.

The antibody described herein can be administered in a therapeutically effective amount. A therapeutically effective amount of an antibody is the amount which is effective, upon single or multiple dose administration to a subject, in treating a subject, e.g., curing, alleviating, relieving or improving at least one symptom of a disorder in a subject to a degree beyond that expected in the absence of such treatment.

Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

In some embodiments, the antibody (e.g., DX-2930) is administered as a single dose, e.g., at 0.1 to 3 mg/kg. In other embodiments, it is administered by multiple doses such as once every 1-4 weeks, e.g., biweekly or by monthly (e.g., every 28 days) administration. Each of the multiple doses can range from 0.1 to 3 mg/kg. In some instances, a patient may be given multiple doses once every 1-4 weeks, e.g., biweekly or monthly, for a suitable period of time, and then followed up with monthly or bi-monthly maintenance treatment at a same or lower dose.

In some embodiments, the patient can be monitored for side effects (e.g., elevation of creatine phosphatase levels) and/or inhibition levels of pKal by the antibody (e.g., serum or plasma concentration of the antibody or the pKal activity level) before and after the treatment or during the course of treatment. If adverse effect is observed, the dose of the antibody might be reduced or the treatment might be terminated. If the inhibition level is below a minimum therapeutic level, further doses of the antibody might be administered to the patient.

In some embodiments, the plasma or serum concentration of the antibody (e.g., DX-2930) may be measured during the course of the treatment (e.g., after the initial dosage) for assessing the efficacy of the treatment. If the plasma or serum concentration of the antibody is lower than about 80 nM, a follow-up dosage may be needed, which may be the same or higher than the initial dosage. The plasma or serum concentration of the antibody may be measured by determining the protein level of the antibody in a plasma or serum sample obtained from the subject, e.g., by an immune assay or MS assay. The plasma or serum concentration of the antibody may also be measured by determining the inhibitory level of pKal in a plasma or serum sample obtained from a subject treated with the antibody. Such assays may include the synthetic substrate assay or the Westernblot assay for measuring cleaved kininogen as described herein.

Alternatively or in addition, the plasma or serum level of creatine kinase can be monitored during the course of the treatment. If the plasma or serum level of creatine kinase is found to elevate during the treatment, the dosage of the antibody may be reduced or the treatment may be terminated.

In some embodiments, an optimal dosage (e.g., optimal prophylactic dosage or optimal therapeutic dosage) of an anti-pKal antibody as described herein (e.g., DX-2930 or an antigen-binding fragment thereof) may be determined as follows. The antibody is given to a subject in need of the treatment at an initial dose. The plasma concentration of the antibody in the subject is measured. If the plasma concentration is lower than 80 nM, the dose of the antibody is increased in a subsequent administration. A dosage of the antibody that maintains the antibody plasma concentration above about 80 nM can be chosen as the optimal dosage for the subject. The cretine phosphokinase level of the subject can be monitored during the course of treatment and the optimal dosage for that subject can be further adjusted based on the cretine phosphokinase level, e.g., the dosage of the antibody might be reduced is elevation of cretine phosphokinase is observed during treatment.

Combination Therapies

An anti-plasma kallikrein antibody described herein can be administered in combination with one or more of the other therapies for treating a disease or condition associated with plasma kallikrein activity, e.g., a disease or condition described herein. For example, a plasma kallikrein binding antibody can be used therapeutically or prophylactically with surgery, another anti- plasma kallikrein Fab or IgG (e.g., another Fab or IgG described herein), another plasma kallikrein inhibitor, a peptide inhibitor, or small molecule inhibitor. Examples of plasma kallikrein inhibitors that can be used in combination therapy with a plasma kallikrein binding antibodies described herein include plasma kallikrein inhibitors described in, e.g., WO 95/21601 or WO 2003/103475.

One or more plasma kallikrein inhibitors can be used in combination with one or more plasma kallikrein binding antibodies described herein. For example, the combination can result in a lower dose of the inhibitor being needed, such that side effects are reduced.

A plasma kallikrein binding antibody described herein can be administered in combination with one or more current therapies for treating HAE. For example, antibody DX-2930 or a functional variant thereof as described herein can be co-used with a second anti-HAE therapeutic agent such as ecallantide, a C1 esterase inhibitor (e.g., CINRYZE), aprotinin (TRASYLOL®), and/or a bradykinin B2 receptor inhibitor (e.g., icatibant (FIRAZYR®)).

The term "combination" refers to the use of the two or more agents or therapies to treat the same patient, wherein the use or action of the agents or therapies overlap in time. The agents or therapies can be administered at the same time (e.g., as a single formulation that is administered to a patient or as two separate formulations administered concurrently) or sequentially in any order. Sequential administrations are administrations that are given at different times. The time between administration of the one agent and another agent can be minutes, hours, days, or weeks. The use of a plasma kallikrein binding antibody described herein can also be used to reduce the dosage of another therapy, e.g., to reduce the side effects associated with another agent that is being administered. Accordingly, a combination can include administering a second agent at a dosage at least 10, 20, 30, or 50% lower than would be used in the absence of the plasma kallikrein binding antibody.

A combination therapy can include administering an agent that reduces the side effects of other therapies. The agent can be an agent that reduces the side effects of a plasma kallikrein associated disease treatment Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Single Ascending Dose Study of DX-2930 in Healthy Volunteers

A single ascending dose study in healthy volunteers was performed using the following doses of DX-2930: 0.1 mg/kg, 0.3 mg/kg, 1 mg/kg, and 3 mg/kg. The data for each volunteer is obtained and analysed to determine the safety of each dose. The heavy and light chain full and variable sequences for DX-2930 are provided below, with signal sequences in italics. The CDRs are boldfaced and underlined.

DX-2930 Heavy Chain Amino Acid Sequence (451 amino acids, 49439.02 Da)

(SEQ ID NO: 1)
*MGWSCILFLVATATGAHS*EVQLLESGGGLVQPGGSLRLSCAASGFTFSHY
IMMWVRQAPGKGLEWVSGIYSSGGITVYADSVKGRFTISRDNSKNTLYLQ
MNSLRAEDTAVYYCAYRRIGVPRRDEFDIWGQGTMVTVSSASTKGPSVFP
LAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCP
PCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSV
MHEALHNHYTQKSLSLSPG

DX-2930 Light Chain Amino Acid Sequence (213 amino acids, 23419.08 Da)

(SEQ ID NO: 2)
*MGWSCILFLVATATGAHS*DIQMTQSPSTLSASVGDRVTITCRASQSISSW
LAWYQQKPGKAPKLLIYKASTLESGVPSRFSGSGSGTEFTLTISSLQPDD
FATYYCQQYNTYWTFGQGTKVEIKRTVAAPSVFIFPPSDEQLKSGTASVV
CLLNNFYPREAKVQWKVDNALQSGNSQESVTEQDSKDSTYSLSSTLTLSK
ADYEKHKVYACEVTHQGLSSPVTKSFNRGEC

DX-2930 Heavy Chain Variable Domain Amino Acid Sequence (SEQ ID NO: 3)
EVQLLESGGGLVQPGGSLRLSCAASGFTFSHYIMMWVRQAPGKGLEWVSG
IYSSGGITVYADSVKGRFTISRDNSKNTLYLQMNSLRAEDTAVYYCAYRR
IGVPRRDEFDIWGQGTMVTVSS DX-2930 Light Chain Variable Domain Amino Acid Sequence (SEQ ID NO: 4)
DIQMTQSPSTLSASVGDRVTITCRASQSISSWLAWYQQKPGKAPKLLIYK
ASTLESGVPSRFSGSGSGTEFTLTISSLQPDDFATYYCQQYNTYWTFGQG
TKVEIK

TABLE 1

| CDRs for DX-2930. | |
|---|---|
| CDR | Amino acid sequence |
| Heavy chain CDR1 | HYIMM (SEQ ID NO: 5) |
| Heavy chain CDR2 | GIYSSGGITVYADSVKG (SEQ ID NO: 6) |
| Heavy chain CDR3 | RRIGVPRRDEFDI (SEQ ID NO: 7) |
| Light chain CDR1 | RASQSISSWLA (SEQ ID NO: 8) |
| Light chain CDR2 | KASTLES (SEQ ID NO: 9) |
| Light chain CDR3 | QQYNTYWT (SEQ ID NO: 10) |

Phase 1a Study Design

This study was randomized, double-blind, and placebo controlled. Single and ascending doses DX-2930 were administered subcutaneously to healthy subjects. Participants were randomly assigned to one of four subject cohorts, each corresponding to a single dose (0.1 mg/kg, 0.3 mg/kg, 1 mg/kg, or 3 mg/kg). Each cohort contained six active drug-treated subjects and two placebo-treated subjects. All subjects were monitored for 16 weeks following the completion of the dosing schedule.

Safety Results

DX-2930 was well-tolerated, without evidence of dose-limiting toxicity, at single doses up to 3.0 mg/kg. Thus, this study yielded no evidence of any clinically significant safety signals related to DX-2930.

Clinical laboratory results demonstrated no clinically significant imbalance between DX-2930 and placebo for any adverse event. Most commonly reported adverse events include headache (25% of DX-2930 treated subjects and 25% of placebo-treated subjects). No adverse event was severe and all adverse events resolved.

Analysis of vital signs, physical examinations, and electrocardiograms (ECGs) demonstrated an upper respiratory infection in one subject who received a dose of 0.1 mg/kg, however, the investigator reported that the infection was mild and unrelated to treatment. Otherwise, there were no observed abnormalities with vital signs, physical examinations, and electrocardiograms (ECGs) of the study subjects.

Anti-drug antibody testing yielded no evidence of seroconversion.

Only two subjects with severe AE were reported as treatment-related by blinded investigator. Creatine phosphokinase elevation of 902 U/L [reference range: 21-215 U/L] was observed in one subject dosed with 0.1 mg/kg DX-2930 (4.2% of all DX-2930 treated subjects). Creatine phosphokinase elevation of 1967 U/L [reference range: 32-294 U/L] was observed in one subject dosed with placebo (12.5% of all placebo-treated subjects). Results demonstrated no lab abnormality associated with any other AE or finding that might indicate clinical importance. There were no injection site reactions in any subject.

TABLE 2

Overview of Safety Data from Phase 1a Study

|  | 0.1 mg/kg (n = 6) | 0.3 mg/kg (n = 6) | 1.0 mg/kg (n = 6) | 3.0 mg/kg (n = 6) | All DX-2930 treated subjects (n = 24) | Placebo (n = 8) |
|---|---|---|---|---|---|---|
| Subjects with AEs | 5 | 3 | 4 | 4 | 16 (66.7%) | 6 (75.0%) |
| Deaths | 0 | 0 | 0 | 0 | 0 | 0 |
| SAEs | 0 | 0 | 0 | 0 | 0 | 0 |
| Discontinuations due to AE | 0 | 0 | 0 | 0 | 0 | 0 |
| Subjects with treatment - related AEs* | 2 | 1 | 1 | 2 | 6 (25.0%) | 4 (50.0%) |

*Treatment-related AEs: Relatedness of AEs to study drug was assessed by a blinded investigator Note:
The term "adverse event" (AE) here refers specifically to a treatment-emergent adverse event. An adverse event was considered treatment-emergent if the onset time is after administration of study drug through the Day 112 post-dosing final follow-up visit or, in the event that onset time precedes study drug administration, the AE increases in severity during the 112 day post-dosing follow-up period.

Pharmacodynamic (PD) and Pharmacokinetic (PK) Results

Table 3 provides the pharmacokinetic parameter estimates for each dose cohort. The mean $C_{max}$ and $AUC_{last}$ values exhibit a strict, linear dose dependence-consistent with a well behaved antibody. Drugs with long half-lives enable infrequent dosing schedules to achieve stable, steady state blood levels. DX-2930 demonstrated a consistent extended half-life of almost three weeks across all dose groups.

A therapeutic candidate for prophylaxis of HAE should have a long half-life and a predictable pharmacokinetic profile to enable infrequent dosing and a logical, technical dosing rationale. DX-2930 provides a consistent pharmacokinetic profile, thereby enabling a determination of a dosing regimen to provide significant therapeutic benefit to patients with HAE.

TABLE 3

| Dose Group (mg/kg) | $C_{max}$ (ng/mL) | $T_{max}$ (days) | $AUC_{last}$ (day * ng/mL) | Vz/F (mL/kg) | CL/F (mL/day/kg) | $T_{1/2}$ (days) |
|---|---|---|---|---|---|---|
| 0.1 | 555 ± 124 | 7 ± 3.85 | 15506 ± 508 | 154 ± 22 | 5.5 ± 1.8 | 20.5 ± 4.4 |
| 0.3 | 1452 ± 664 | 8.4 ± 3.1 | 39070 ± 13528 | 182 ± 70 | 7.7 ± 3.4 | 16.7 ± 2.0 |
| 1.0 | 5612 ± 2422 | 8.5 ± 6.25 | 167570 ± 55562 | 170 ± 73 | 6.5 ± 2.5 | 18.9 ± 6.3 |
| 3.0 | 14548 ± 5224 | 6.67 ± 0.82 | 512746 ± 208384 | 187 ± 79 | 6.6 ± 2.7 | 20.4 ± 4.6 |

Figure 7:
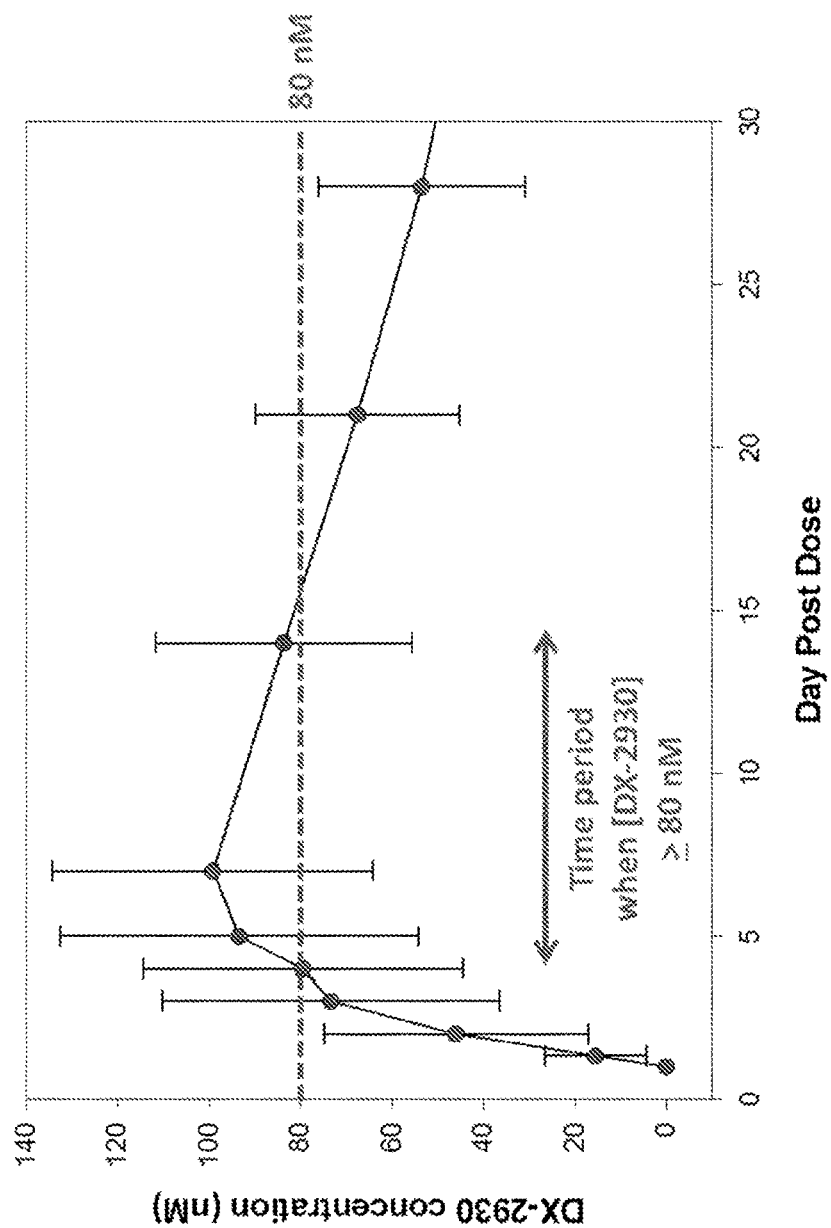
FIG. 7 is a graph demonstrating that plasma drug levels at or above 80 nM were attained following administration of a single dose 3 mg/kg of DX-2930.

Pharmacokinetic (PK) parameters of DX-2930 were evaluated following a single dose in healthy subjects. Following a single 3 mg/kg dose, plasma drug concentrations exceeding the target level of 80 nM were attained. Drug levels either around or greater than 80 nM were maintained for approximately 10 days (FIG. 7). Drug levels will continue to accumulate upon repeated administration of the drug until steady state is reached. Even following only a single dose of DX-2930, drug levels exceeding the target of 80 nM were attained and maintained for a prolonged period of time. The PK data from this study support the feasibility of a dosing strategy to attain plasma drug concentrations above the targeted 80 nM level and to then continually maintain them. Furthermore, higher drug levels beyond 80 nM may be achieved if necessary to attain sufficient plasma kallikrein inhibition relevant to HAE prophylaxis.

Pharmacodynamic (PD) assessment of DX-2930 was performed. To further characterize DX-2930, exploratory biomarker assays were performed ex vivo on subjects' plasma samples to evaluate the pharmacodynamic profile of the molecule. Two independent assays were conducted- a plasma kallikrein activity assay using an artificial fluorogenic substrate and a Western blot assay measuring the cleavage of kininogen, the native substrate of plasma kallikrein from which bradykinin is generated.

These assays are semi-quantitative. Data points should therefore be interpreted relative to other data points within that experiment and not compared across the assays or to other assay systems. These assays are conducted in normal subject plasma with normal levels of C1-inhibitor. Consequently, the healthy subjects used in these biomarker assays do not develop HAE attacks. The goal of these biomarker assessments was to confirm that DX-2930 in plasma from dosed subjects has inhibitory activity against plasma kallikrein. Equally important, these studies were performed to assess whether the pharmacodynamic results corroborated the observed PK profile.

Figure 9:
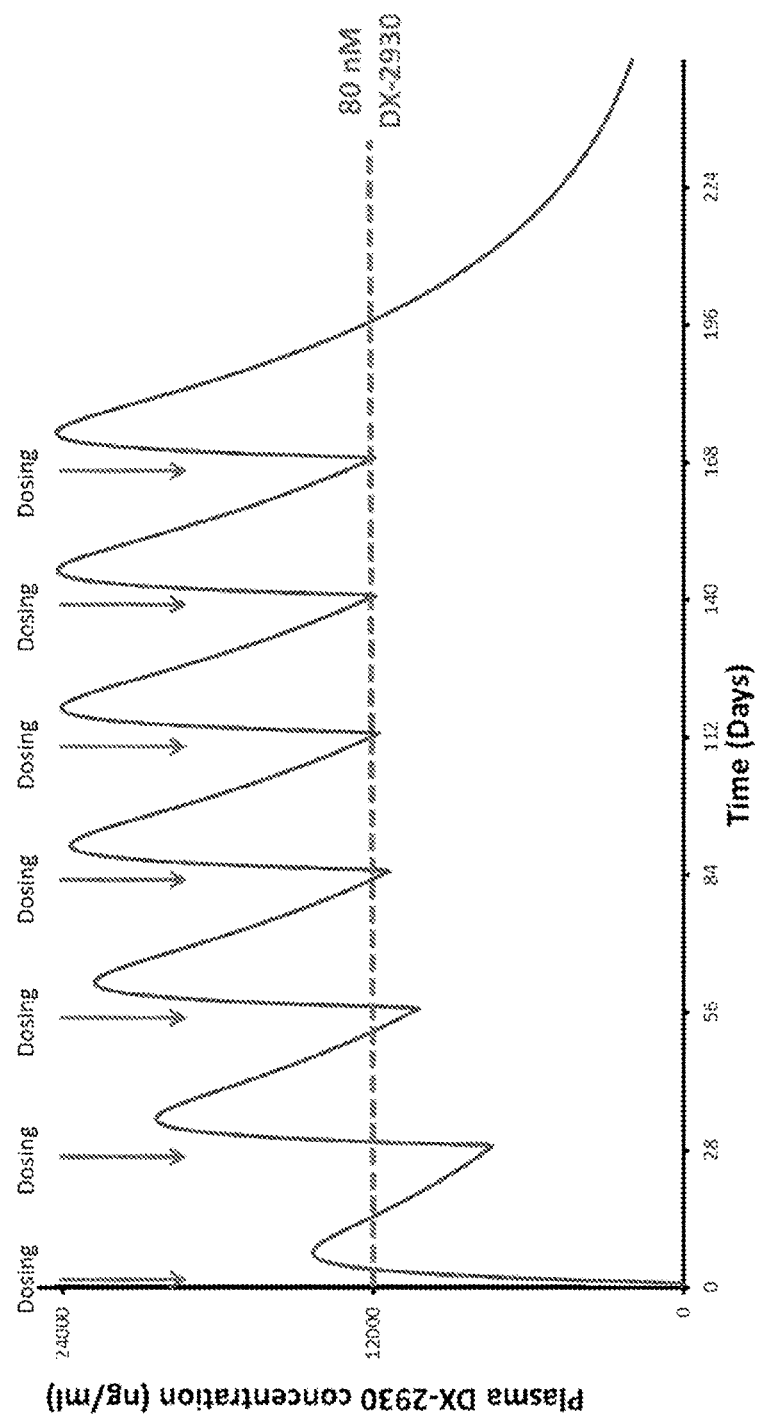
FIG. 9 is a graph depicting a pharmacodynamic (PD) effect of DX-2930 at 3 mg/kg SC every 28 days in healthy subjects.
Figure 10:
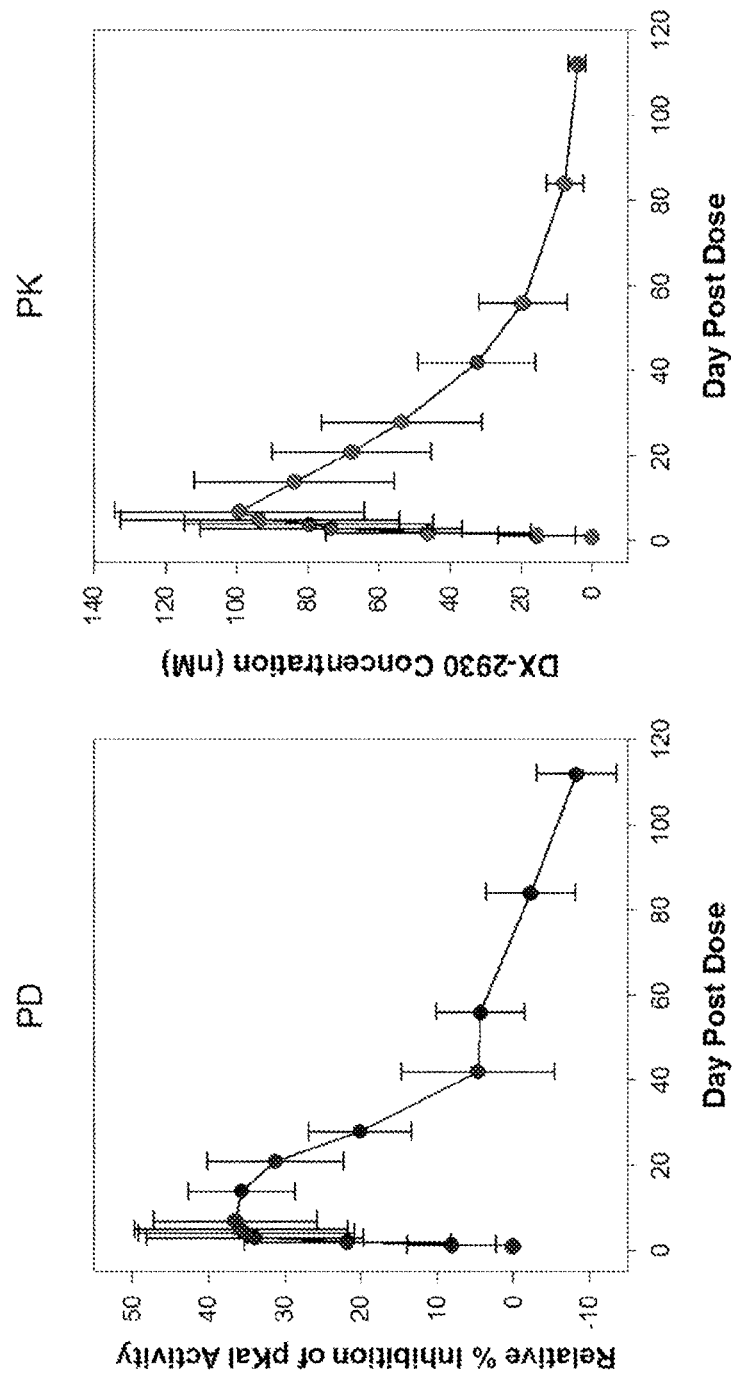
FIG. 10 is a graph depicting pharmacodynamic (PD) and pharmacokinetic (PK) data following a single dose (3 mg/kg) of DX-2930. PD data plotted as the relative % inhibition of pKal activity over time. PK data plotted as the plasma DX-2930 concentration (nM) over time. *: P value <0.05 for 3 mg/kg on day 5 vs placebo.
Figure 11:
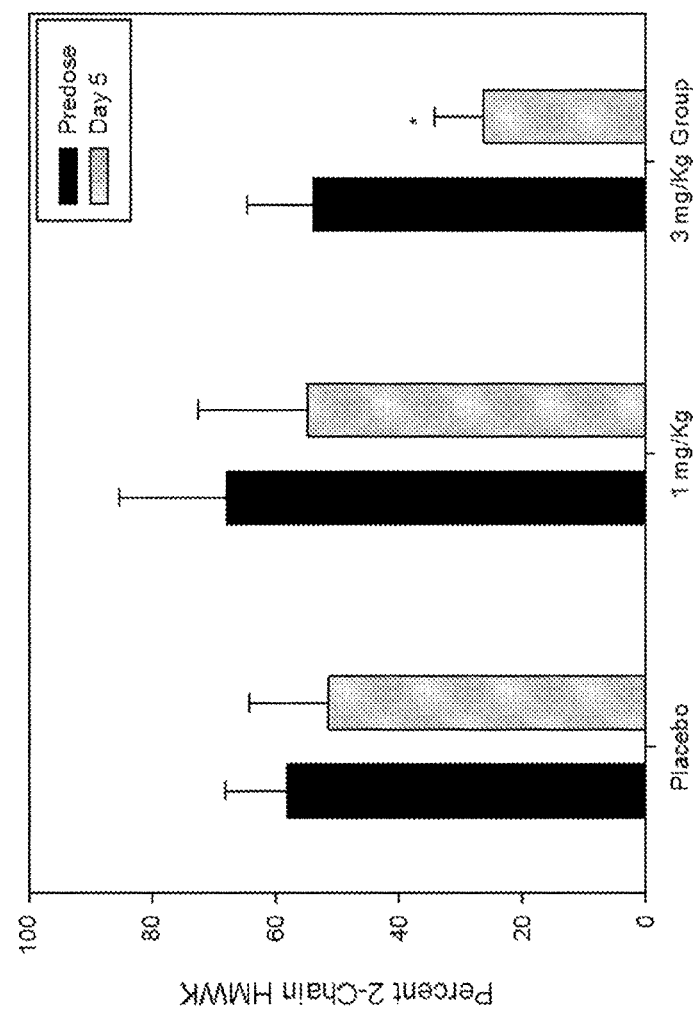
FIG. 11 is a graph depicting the pharmacodynamics (PD) activity of DX-2930 against a native biological substrate (HMWK cleavage measured as generation of 2-chain HMWK).
Figure 12:
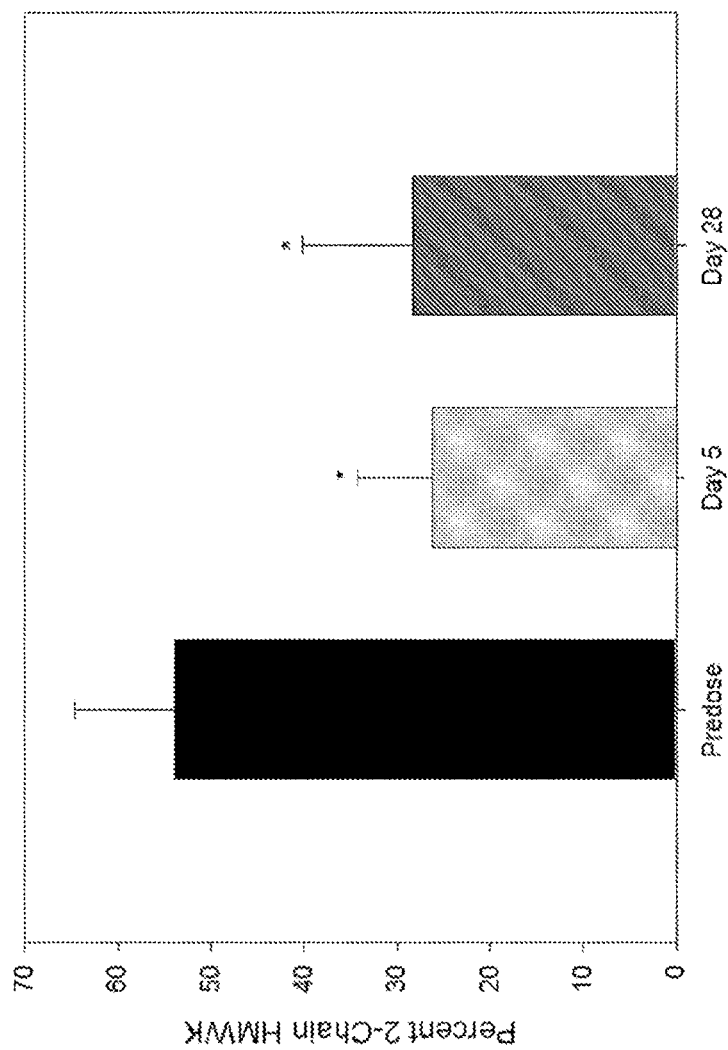
FIG. 12 is a graph depicting sustained DX-2930 bioactivity over time following a single administration of 3 mg/kg of DX-2930. *: P value<0.05 for 3 mg/kg and day 28 vs predose.

FIG. 9 depicts the pharmacodynamics effects of DX-2930. Plasma from study drug-treated subjects was activated ex vivo to induce the contact system pathway and thereby stimulate plasma kallikrein generation and activity. pKal activity was measured via a fluorogenic assay. Data from the 1 and 3 mg/kg groups are displayed. Plasma kallikrein inhibition was clearly evident, particularly in the 1 and 3 mg/kg dose groups. No appreciable inhibition was observed in the 0.1 mg/kg or placebo groups. The observed inhibition was both dose and time-dependent and confirms the inhibitory activity of DX-2930. The PD effect of DX-2930 corroborates the PK data for DX-2930.

Therapeutic Use of DX-2930

For effective prophylaxis, a requirement for effectiveness is that the relevant drug target be inhibited at a level above the minimum required amount on a continual basis. Gaps in inhibition coverage be minimized or avoided altogether. When the level of inhibition drops below the minimum required level, the individual is biologically vulnerable for activation of the pathologic process and may be placed at risk clinically for the disease event.

HAE is not exempt from widely established principles of prophylaxis. In HAE, plasma kallikrein represents a validated drug target that is critical to the pathogenesis of angioedema attacks. Preventing HAE attacks may require that plasma kallikrein inhibition be continually maintained above the minimum therapeutic level. Gaps in coverage over time be minimized to avoid periods of vulnerability. This need is further emphasized by the phenomenon of a positive feedback loop that is hypothesized to play an important role in HAE attacks. Upon initiation of this cascade, activation of plasma kallikrein leads to Factor XII activation that in turn drives more plasma kallikrein generation.

The inhibition of plasma kallikrein by DX-2930 and ecallantide, a known therapeutic approved in the U.S. for acute treatment of HAE attacks, were compared in an in vitro assay. In this system, human plasma was exposed to an agent that initiates the contact system and converts prekallikrein to active plasma kallikrein.

Figure 5:
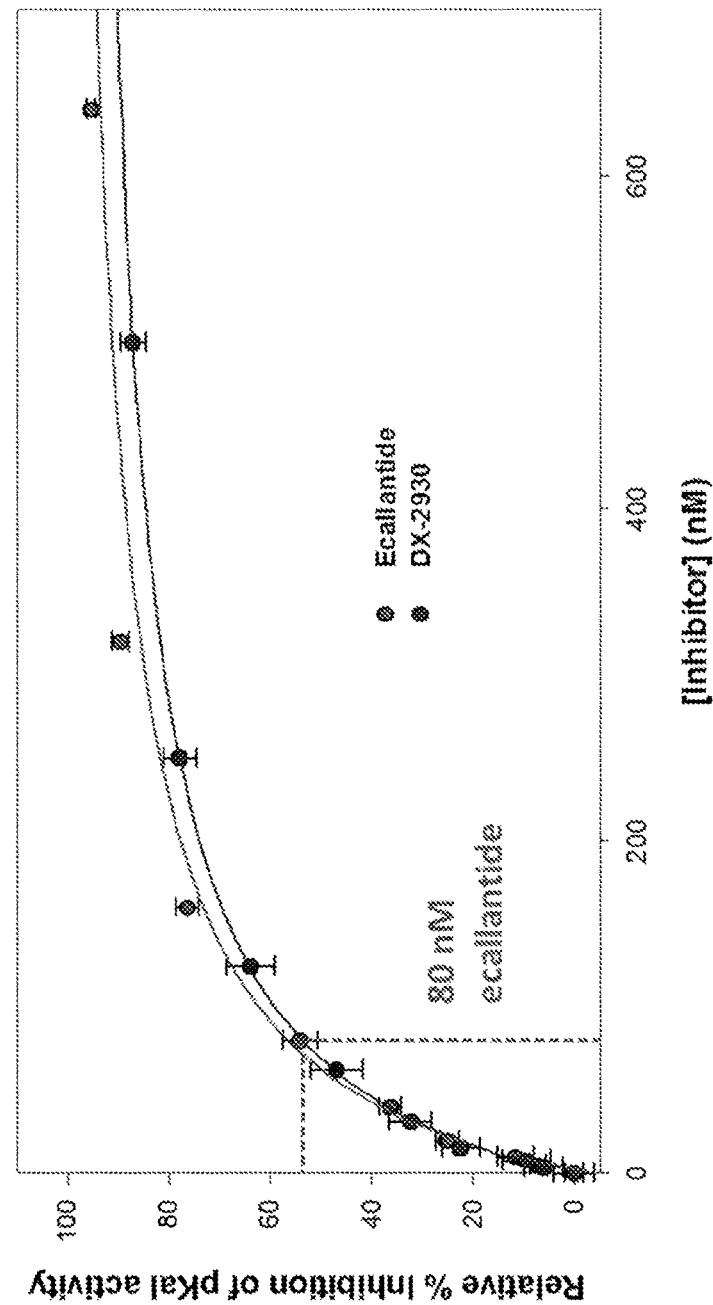
FIG. 5 is a graph depicting the comparative inhibitory activity of DX-2930 and ecallantide against pKal in vitro.
Figure 6:
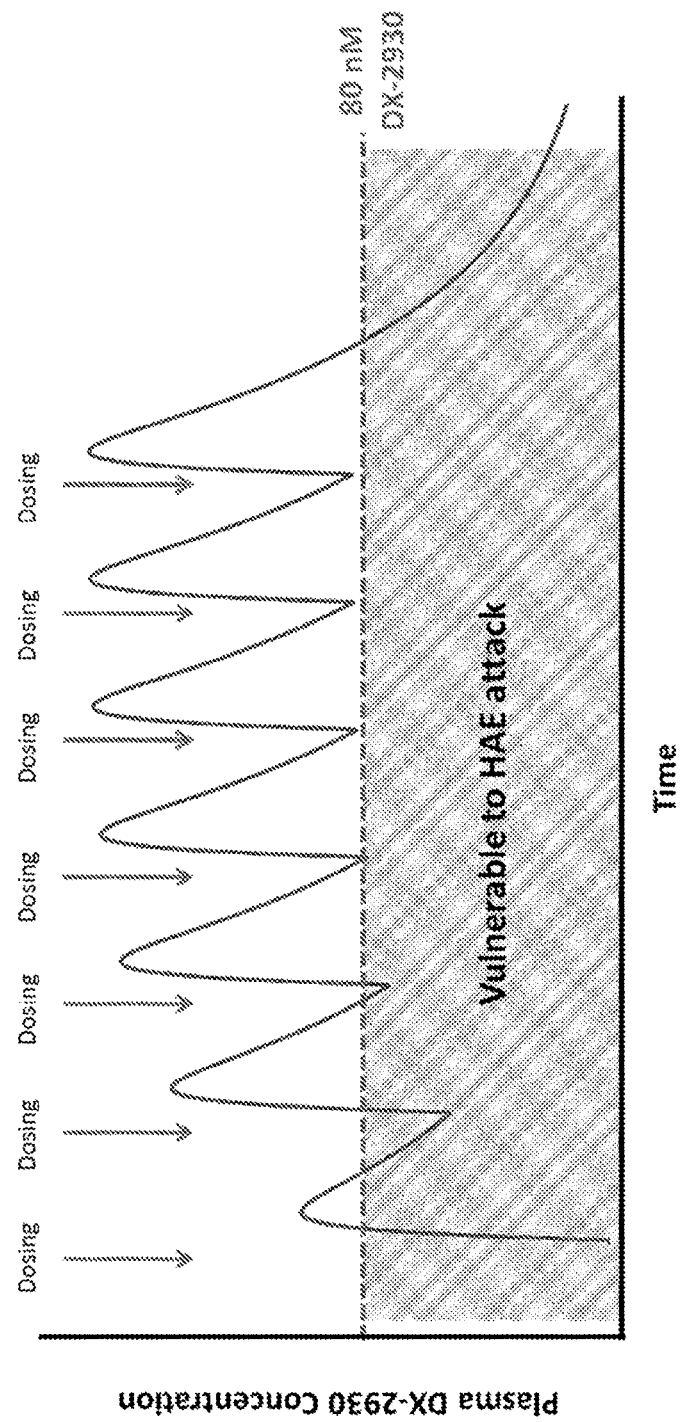
FIG. 6 is a graph depicting alternative hypotheses regarding a requirement of continually maintaining a DX-2930 plasma concentration at or above 80 nM for the treatment and/or prophylaxis of HAE. Alternatively, the required DX-2930 plasma concentration may be lower or higher than 80 nM for the treatment and/or prophylaxis of HAE.

The peak concentration of ecallantide in the plasma following dosing in patients, 80 nM, provides only partial inhibition of plasma kallikrein activity. Around this concentration range of 80 nM, these assay results show that DX-2930 has potency comparable to ecallantide (FIG. 5). Given that 80 nM appears to be the plasma kallikrein level relevant for HAE attacks and given the comparable potency of DX-2930 with ecallantide in inhibiting plasma kallikrein at this concentration range, it is hypothesized that maintaining DX-2930 continually above a plasma drug concentration of 80 nM would prevent HAE attacks (FIG. 6). The 80 nM target for DX-2930 plasma drug levels appears to be robust based upon currently available data and understanding of disease biology. Although 80 nM is an initial target, it is possible that lower or higher drug levels of DX-2930 may be necessary to attain the therapeutic dose.

Example 2

Multiple Ascending Dose Study of DX-2930 in HAE Patients

Figure 2:
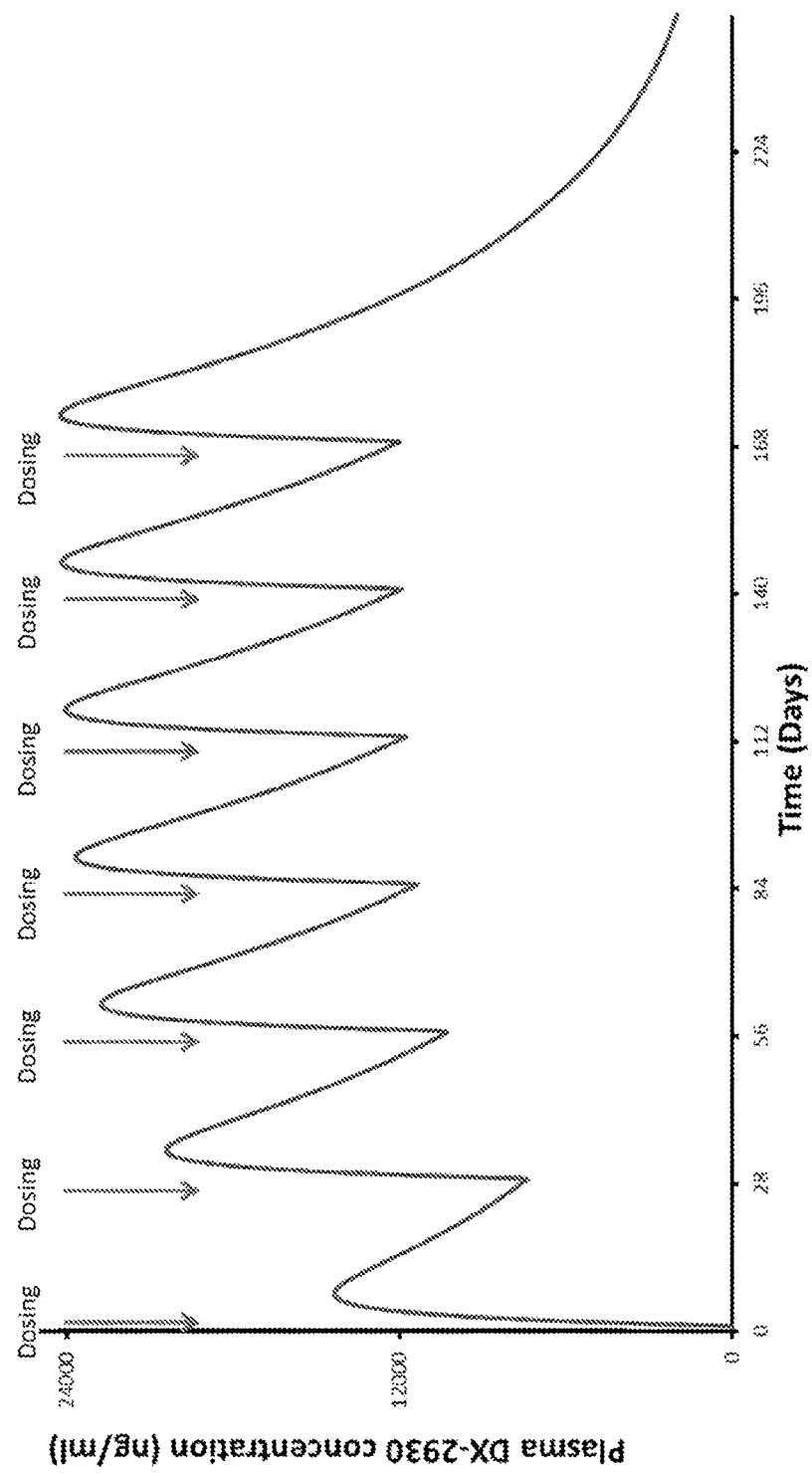
FIG. 2 is a graph depicting predicted plasma concentrations following repeat dosing with 3 mg/kg DX-2930 via subcutaneous administration every 28 days in healthy subjects.
Figure 3:
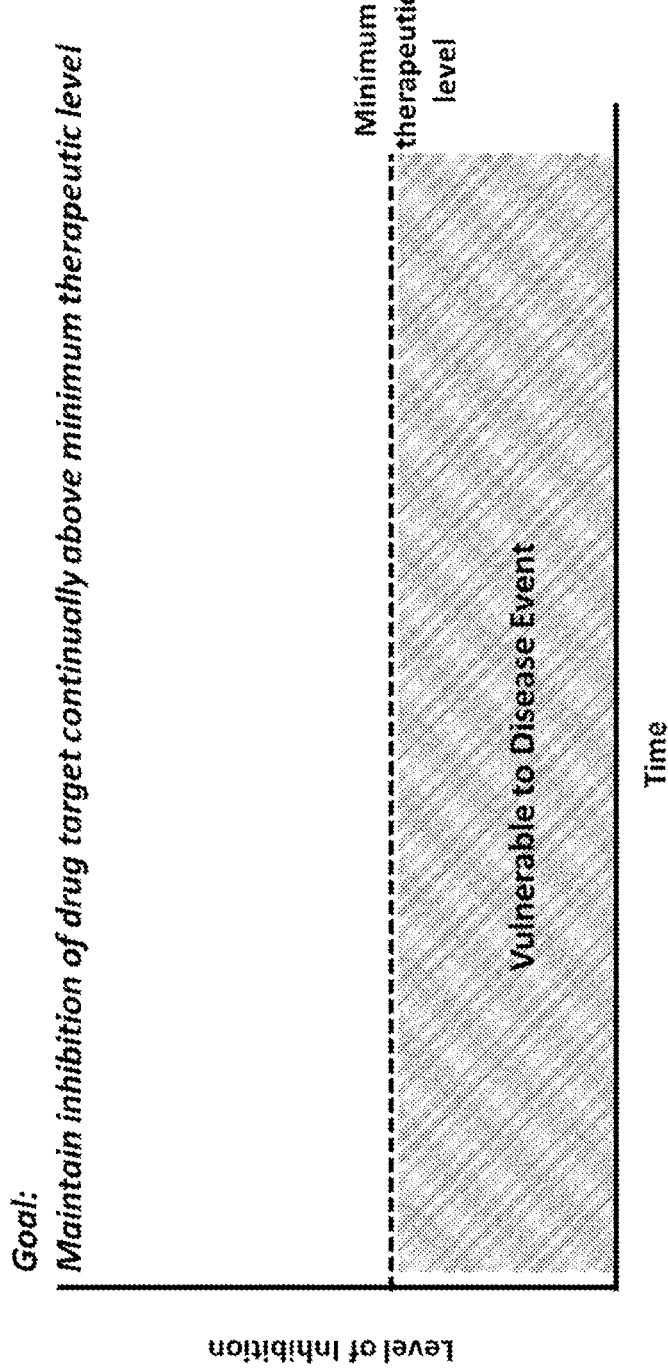
FIG. 3 is a graph depicting the general principles of the use of a medicament for prophylaxis of a disease condition.
Figure 4:
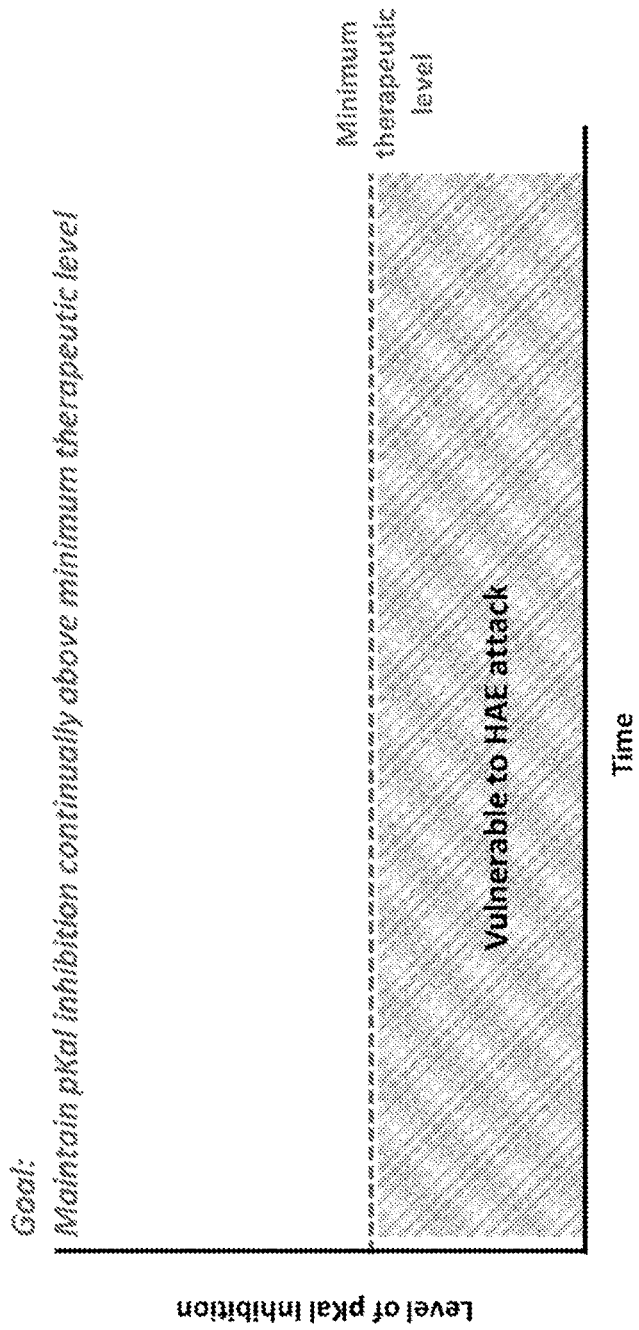
FIG. 4 is a graph depicting the general principles of the use of DX-2930 for prophylaxis of HAE.

Multiple doses of DX-2930 are administered to HAE patients at the following dosages: 0.1 mg/kg, 0.3 mg/kg, 1 mg/kg, or 3 mg/kg. FIG. 2 provides a predicted plasma concentrations that would be achieved following repeat dosing of the 3 mg/kg dose of DX-2930. The initial concentration profile is consistent with the profile observed upon single dose administration in healthy subjects.

Figure 8:
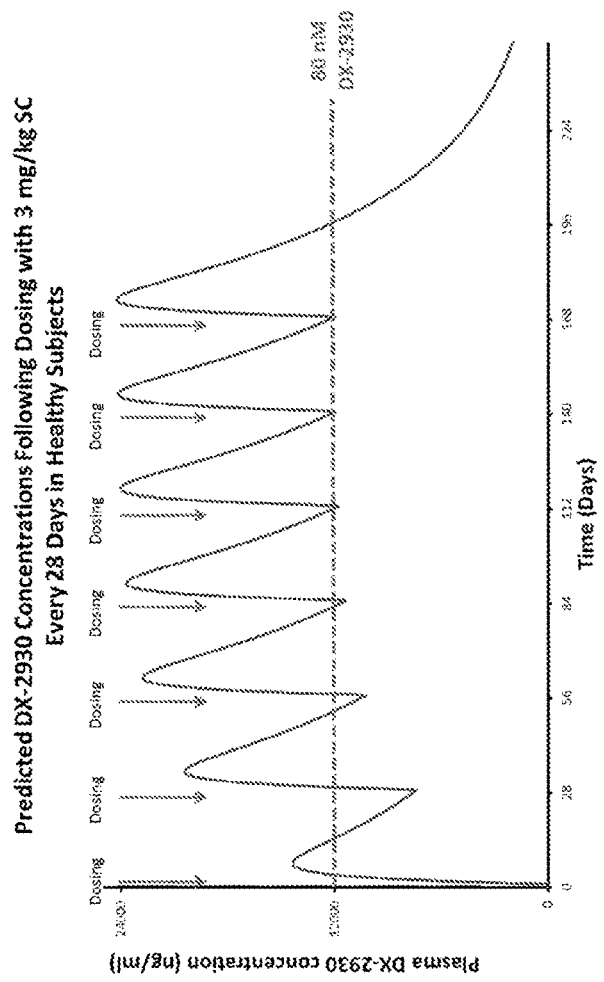
FIG. 8 is a graph depicting pharmacokinetic (PK) modeling of chronic DX-2930 dosing at 3 mg/kg delivered subcutaneously every 28 days in healthy subjects.

PK modeling can be performed to predict pharmacodynamic and pharmacokinetic behavior of DX-2930 following chronic dosing. FIG. 8 represents a hypothetical scenario in which DX-2930 is dosed at 3 mg/kg every 28 days in healthy subjects. Results of this modeling suggest that after the steady state has been attained, repeat administrations will continually maintain drug concentrations around or above the initially targeted 80 nM level (see Example 2 for discussion of this threshold value).

The safety and efficacy of DX-2930 in HAE patients is assessed following two administrations of DX-2930 given one week apart. Biomarker data (along with pharmokinetics) are assessed to determine which dosage(s) to use for a follow-up study to evaluate the efficacy of DX-2930 (at different doses) in preventing HAE attacks.

Example 3

Pharmacologic Modeling of Dosing Regimen in Investigating Long-Term Prophylaxis of Hereditary Angioedema Methods In vitro inhibition of pKal by ecallantide and DX-2930 was assessed using a synthetic substrate assay. Modeling was conducted using pharmacokinetic (PK) data from a single ascending dose study of subcutaneous DX-2930 in healthy subjects.

Results

In an in vitro pKal assay, DX-2930 and ecallantide displayed comparable pharmacodynamic (PD) activity at 80 nM concentrations. The plasma concentration of a pKal inhibitor below 80 nM might offer only partial prophylactic effect, lending further credence to the mid- and high-dose hypotheses over the low-dose hypothesis. Thus, continually maintaining DX-2930 drug levels above 80 nM should attain the level of pKal inhibition delineated by the mid-dose hypothesis. PK modeling indicated that chronic DX-2930 dosing would yield steady state plasma drug concentrations above 80 nM with 100 mg every 2 weeks (or 300 mg every 4 weeks) and above 200 nM with 300 mg every 2 weeks.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims

What is claimed is:

1. A method of treating hereditary angioedema (HAE), the method comprising:
   administering to a subject in need thereof an antibody in an effective amount of 300 mg or 400 mg every two weeks or every four weeks, wherein the antibody comprises:
   a heavy chain CDR1 comprising HYIMM (SEQ ID NO:5);
   a heavy chain CDR2 comprising GIYSSGGITVY-ADSVKG (SEQ ID NO:6);
   a heavy chain CDR3 comprising RRIGVPRRDEFDI (SEQ ID NO:7);
   a light chain CDR1 comprising RASQSISSWLA (SEQ ID NO:8);
   a light chain CDR2 comprising KASTLES (SEQ ID NO:9); and
   a light chain CDR3 comprising QQYNTYWT (SEQ ID NO:10).

2. The method of claim 1, wherein the antibody is a full length antibody or an antigen-binding fragment thereof.

3. The method of claim 2, wherein the antibody is DX-2930.

4. The method of claim 1, wherein the antibody is administered at 300 mg every two weeks.

5. The method of claim 1, wherein the antibody is administered at 300 mg every four weeks.

6. The method of claim 1, wherein the antibody is administered subcutaneously.

7. The method of claim 1, wherein the subject is a human patient having, suspected of having, or at risk for HAE.

8. The method of claim 1, wherein the antibody is administered for prophylactic treatment.

9. The method of claim 1, further comprising monitoring the level of creatine phosphokinase in the subject before and after the treatment, or during the course of the treatment.

10. The method of claim 9, further comprising reducing the dose of the antibody or terminating the treatment if creatine phosphokinase elevation is observed.

11. The method of claim 1, wherein the antibody is an IgG1.

12. The method of claim 1, wherein the antibody comprises a heavy chain variable region comprising the sequence of SEQ ID NO:3 and a light chain variable region comprising the sequence of SEQ ID NO:4.

13. The method of claim 4, wherein the antibody comprises a heavy chain variable region comprising the sequence of SEQ ID NO:3 and a light chain variable region comprising the sequence of SEQ ID NO:4.

14. The method of claim 5, wherein the antibody comprises a heavy chain variable region comprising the sequence of SEQ ID NO:3 and a light chain variable region comprising the sequence of SEQ ID NO:4.

15. The method of claim 1, wherein the antibody comprises a heavy chain comprising the sequence of SEQ ID NO:1 and a light chain comprising the sequence of SEQ ID NO:2.

16. The method of claim 4, wherein the antibody comprises a heavy chain comprising the sequence of SEQ ID NO:1 and a light chain comprising the sequence of SEQ ID NO:2.

17. The method of claim 5, wherein the antibody comprises a heavy chain comprising the sequence of SEQ ID NO:1 and a light chain comprising the sequence of SEQ ID NO:2.

* * * * *

UNITED STATES PATENT AND TRADEMARK OFFICE
CERTIFICATE OF CORRECTION

PATENT NO. : 11,084,884 B2  
APPLICATION NO. : 15/113297  
DATED : August 10, 2021  
INVENTOR(S) : Daniel J. Sexton et al.

Page 1 of 1

It is certified that error appears in the above-identified patent and that said Letters Patent is hereby corrected as shown below:

On the Title Page

At item (71), the Applicant "Takeda Pharmaceutical Company Limited, Osaka (JP)" should be replaced with --Dyax Corp., Lexington, MA (US)--.

At item (72), the place of residence of Inventor Joseph Biedenkapp "Newton, MA (US)" should be replaced with --Acton, MA (US)--.

Signed and Sealed this  
Eighteenth Day of January, 2022

Drew Hirshfeld  
*Performing the Functions and Duties of the*  
*Under Secretary of Commerce for Intellectual Property and*  
*Director of the United States Patent and Trademark Office*